(12) United States Patent
Scherman et al.

(10) Patent No.: US 6,300,321 B1
(45) Date of Patent: Oct. 9, 2001

(54) COMPOUNDS, PREPARATION AND USE FOR TRANSFERRING NUCLEIC ACIDS INTO CELLS

(75) Inventors: Daniel Scherman, Paris; Catherine Dubertret, Sevres, both of (FR); Gerardo Byk, Oyriat Ono (IL)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/424,380

(22) PCT Filed: May 25, 1998

(86) PCT No.: PCT/FR98/01041
§ 371 Date: Dec. 15, 1999
§ 102(e) Date: Dec. 15, 1999

(87) PCT Pub. No.: WO98/54130
PCT Pub. Date: Dec. 3, 1998

(30) Foreign Application Priority Data

May 28, 1997 (FR) .................................................. 97 06549

(51) Int. Cl.⁷ ......................... A61K 31/70; A01N 43/04; C12Q 1/68; C12N 15/85; C12N 15/86

(52) U.S. Cl. ................................ 514/44; 435/6; 435/325; 435/455; 435/458; 424/450

(58) Field of Search .............................. 536/23.1; 514/44; 435/6, 455, 325, 458; 424/450

(56) References Cited

FOREIGN PATENT DOCUMENTS

| WO95/14381 | * | 6/1995 | (WO) . |
| WO96/01840 | * | 1/1996 | (WO) . |
| WO96/01841 | * | 1/1996 | (WO) . |
| WO96/17823 | * | 6/1996 | (WO) . |
| WO96/25508 | * | 8/1996 | (WO) . |
| WO97/18185 | * | 5/1997 | (WO) . |
| WO97/31935 | * | 9/1997 | (WO) . |

* cited by examiner

*Primary Examiner*—John L. LeGuyader
*Assistant Examiner*—Janet Epps
(74) *Attorney, Agent, or Firm*—Karen I. Krupen

(57) ABSTRACT

The invention concerns compounds for transferring nucleic acids into cells. The compounds are more particularly related to the lipopolyamine family, and comprise amidine functions. The compounds are useful for transferring nucleic acids of interest into various cellular types, in vitro, in vivo, or ex vivo.

35 Claims, 11 Drawing Sheets

Compound 1

Figure 1:
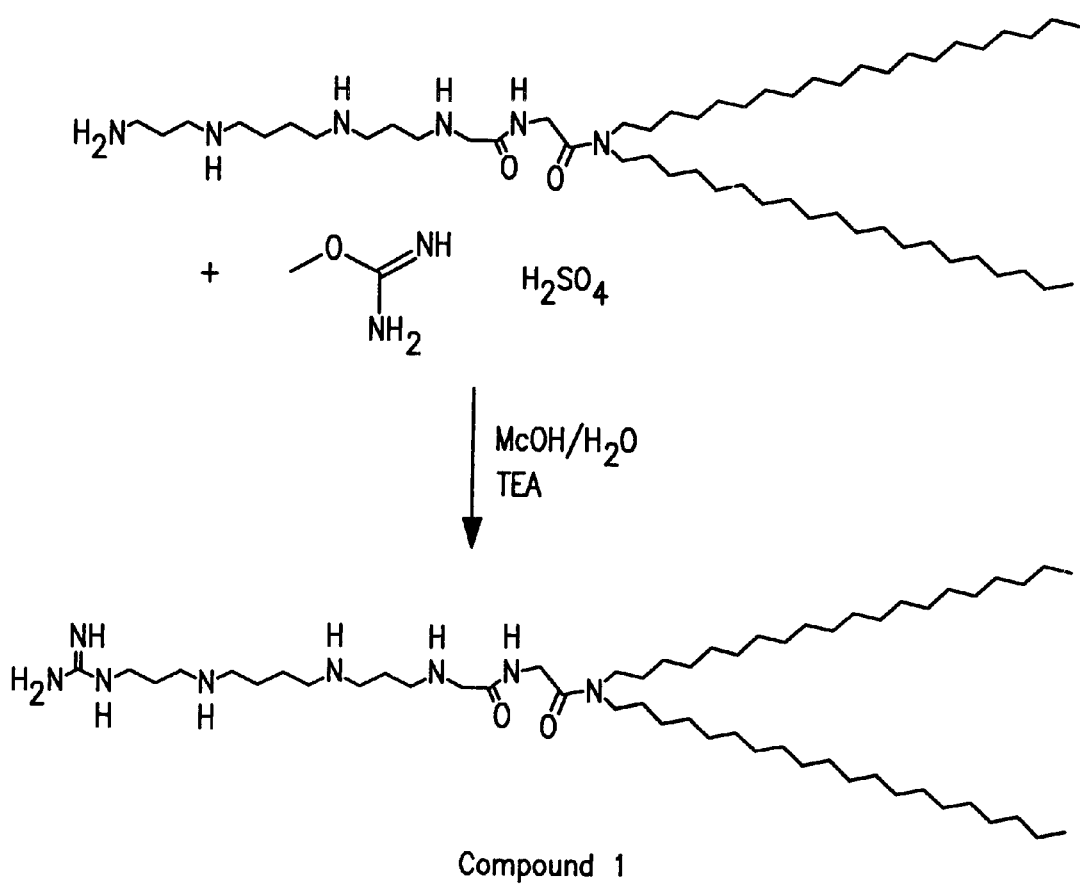

| Charge ratio | 0.25 | 0.5 | 0.75 | 1 | 1.5 | 2 | 3 | 4 | 6 | 8 | 10 | 12 |
|---|---|---|---|---|---|---|---|---|---|---|---|---|
| Micelle | A | A | A | B | B | B | B | B | C | C | C | C |
| with DOPE | A | A | A | B | B | B | B | B | C | C | C | C |
| with Cholesterol | A | A | A | B | B | B | B | B | C | C | C | C |

Compound 2

| Charge ratio | 0.25 | 0.5 | 0.75 | 1 | 1.5 | 2 | 3 | 4 | 6 | 8 | 10 | 12 |
|---|---|---|---|---|---|---|---|---|---|---|---|---|
| Micelle | A | A | A | A | A | A | B | B | B | B | B | B |
| with DOPE | A | A | A | A | A | A | A | B | B | B | C | C |
| with Cholesterol | A | A | A | A | A | A | B | B | B | C | C | C |

Amine-containing analogue

FIG. 8

| Charge ratio | 0.25 | 0.5 | 0.75 | 1 | 1.5 | 2 | 3 | 4 | 6 | 8 | 10 | 12 |
|---|---|---|---|---|---|---|---|---|---|---|---|---|
| Micelle | A | B | B | C | C | C | C | C | C | C | C | C |
| with DOPE | A | A | B | C | C | C | C | C | C | C | C | C |
| with Cholesterol | A | A | B | B | C | C | C | C | C | C | C | C |

Compound 3

| Charge ratio | 0.25 | 0.5 | 0.75 | 1 | 1.5 | 2 | 3 | 4 | 6 | 8 | 10 | 12 |
|---|---|---|---|---|---|---|---|---|---|---|---|---|
| Micelle | A | A | A | A | A | B | B | B | C | C | C | C |
| with DOPE | A | A | A | A | A | B | B | B | B | C | C | C |
| with Cholesterol | A | A | A | A | A | A | B | B | B | C | C | C |

Amine-containing analogue

FIG. 9

| Charge ratio | 0.25 | 0.5 | 0.75 | 1 | 1.5 | 2 | 3 | 4 | 6 | 8 | 10 | 12 |
|---|---|---|---|---|---|---|---|---|---|---|---|---|
| Micelle | A | A | B | B | C | C | C | C | C | C | C | C |
| with DOPE | A | A | B | B | B | C | C | C | C | C | C | C |
| with Cholesterol | A | A | A | B | B | B | C | C | C | C | C | C |

Compound 5

| Charge ratio | 0.25 | 0.5 | 0.75 | 1 | 1.5 | 2 | 3 | 4 | 6 | 8 | 10 | 12 |
|---|---|---|---|---|---|---|---|---|---|---|---|---|
| Micelle | A | A | A | A | A | B | B | C | C | C | C | C |
| with DOPE | A | A | A | A | A | B | C | C | C | C | C | C |
| with Cholesterol | A | A | A | A | A | B | B | C | C | C | C | C |

Amine-containing analogue

FIG. 10

| Charge ratio | 0.25 | 0.5 | 0.75 | 1 | 1.5 | 2 | 3 | 4 | 6 | 8 | 10 | 12 |
|---|---|---|---|---|---|---|---|---|---|---|---|---|
| Micelle | A | B | C | C | C | C | C | C | C | C | C | C |
| with DOPE | A | B | C | C | C | C | C | C | C | C | C | C |
| with Cholesterol | A | B | B | C | C | C | C | C | C | C | C | C |

Compound 6

| Charge ratio | 0.25 | 0.5 | 0.75 | 1 | 1.5 | 2 | 3 | 4 | 6 | 8 | 10 | 12 |
|---|---|---|---|---|---|---|---|---|---|---|---|---|
| Micelle | A | A | A | B | C | C | C | C | C | C | C | C |
| with DOPE | A | A | A | B | C | C | C | C | C | C | C | C |
| with Cholesterol | A | A | A | B | B | B | B | C | C | C | C | C |

Amine-containing analogue

FIG. 11

| Ratio | 0.5 | 0.75 | 1 | 1.5 | 2 | 3 | 4 | 6 |
|---|---|---|---|---|---|---|---|---|
| Compound 2 (micelles) | 35.7% | 27.8% | 20.6% | 21.4% | 19.8% | 19.8% | 19.8% | 19.8% |
| Compound 3 (micelles) | 19.0% | 21.4% | 19.0% | 19.8% | 19.8% | 19.0% | – | – |
| Compound 5 (micelles) | 19.0% | 21.4% | 19.0% | 19.8% | 19.8% | 19.0% | – | – |
| Compound 6 (micelles) | 20.6% | 20.6% | 19.0% | 19.0% | 19.0% | 19.0% | – | – |

FIG. 12

| Ratio | 0.5 | 0.75 | 1 | 1.5 | 2 | 3 | 4 | 6 |
|---|---|---|---|---|---|---|---|---|
| Compound 2 (+cholesterol) | 34.1% | 29.4% | 23.0% | 20.6% | 21.4% | 21.4% | 20.6% | 20.6% |
| Compound 3 (+cholesterol) | 23.8% | 19.8% | 21.4% | 19.8% | 19.8% | 19.8% | – | – |
| Compound 5 (+cholesterol) | 31.0% | 22.2% | 22.2% | 22.2% | 20.6% | 20.6% | 20.6% | 20.6% |
| Compound 6 (+cholesterol) | 19.8% | 20.6% | 19.0% | 19.0% | 19.0% | 19.0% | 19.0% | – |

FIG. 13

| Ratio | 0.5 | 0.75 | 1 | 1.5 | 2 | 3 | 4 | 6 |
|---|---|---|---|---|---|---|---|---|
| Compound 2 (+DOPE) | 31.7% | 27.8% | 26.2% | 23?0% | 20?6% | 19.0% | 19.0% | 19.0% |
| Compound 3 (+DOPE) | 26.2% | 19.8% | 22.2% | 19.8% | 19.8% | 19.8% | 19.8% | – |
| Compound 5 (+DOPE) | 38.1% | 33.3% | 24.6% | 20.6% | 22.2% | 20.6% | 20.6% | – |
| Compound 6 (+DOPE) | 23.0% | 19.8% | 19.8% | 19.8% | 19.8% | 19.8% | 19.8% | – |

FIG. 14

SEQUENCE LISTING

<160> NUMBER OF SEQ ID NOS: 2

<210> SEQ ID NO 1
<211> LENGTH: 9
<212> TYPE: PRT
<213> ORGANISM: ARTIFICIAL SEQUENCE
<220> FEATURE:
<221> NAME/KEY: PEPTIDE

```
<222> LOCATION: (1)..(9)
<223> OTHER INFORMATION: Peptide Functions as Adjuvant

<400> SEQUENCE: 1

Lys Thr Pro Lys Lys Ala Lys Lys Pro
1               5

<210> SEQ ID NO 2
<211> LENGTH: 8
<212> TYPE: PRT
<213> ORGANISM: ARTIFICIAL SEQUENCE
<220> FEATURE:
<221> NAME/KEY: PEPTIDE
<222> LOCATION: (1)..(8)
<223> OTHER INFORMATION: Peptide Functions As Adjuvant

<400> SEQUENCE: 2

Ala Thr Pro Ala Lys Lys Ala Ala
1               5
```

COMPOUNDS, PREPARATION AND USE FOR TRANSFERRING NUCLEIC ACIDS INTO CELLS

This application is a US National Stage application of co-pending PCT application PCT/FR98/01041, filed May 25, 1998. This application also claims the benefit of foreign priority under 35 U.S.C. § 119(a) to application FR97/06549, filed May 28, 1997 in France.

The present invention relates to new compounds for transferring nucleic acids into cells. These new compounds are more particularly related to the lipopolyamine family and contain amidine functional groups. These compounds can be used for transferring nucleic acids of interest into various cell types, both in vitro and in vivo or ex vivo.

With the development of biotechnology, the possibility of effectively transferring nucleic acids into cells has become a necessity. It may involve the transfer of nucleic acids into cells in vitro, for example, for the production of recombinant proteins, or in the laboratory for studying the regulation of the expression of genes, the cloning of genes, or any other manipulation involving DNA. It may also involve the transfer of nucleic acids into cells in vivo, for example for the creation of transgenic animals, the production of vaccines, labelling studies or also therapeutic approaches. It may also be the transfer of nucleic acids into cells ex vivo, in approaches including bone marrow transplants, immunotherapy or other methods involving the transfer of genes into cells collected from an organism for the purpose of their subsequent readministration.

Various types of synthetic vector have been developed to improve the transfer of nucleic acids into cells. Among these vectors, cationic lipids possess advantageous properties. These vectors consist of a cationic polar part which interacts with the nucleic acids, and a hydrophobic lipid part which promotes cellular penetration. Specific examples of cationic lipids are in particular the monocationic lipids (DOTMA: Lipofectin®); some cationic detergents (DDAB); lipopolyamines, and in particular dioctadecylamidoglycyl spermine (DOGS) or 5-carboxyspermylamide of palmitoylphosphatidylethanolamine (DPPES), whose preparation has been described, for example, in Patent Application EP 394 111. Another lipopolyamine family is represented by the compounds described in Patent Application WO 97/18185, incorporated into the present by way of reference.

The present invention relates to a new type of agent for transferring nucleic acids, possessing particularly advantageous properties. More precisely, the compounds according to the present invention are cationic lipids carrying a novel cationic region, conferring improved properties on the molecules. This cationic part is represented more precisely by a particular polyamine, carrying one or more amidine functional groups.

A first subject of the invention relates more precisely to compounds in D, L or DL form, as well as its salts, of general formula (I):

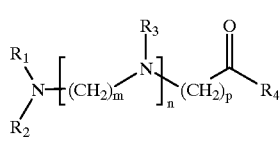

(I)

in which:
R₁, R₂ and R₃ represent, independently of each other, a hydrogen atom or a group —(CH₂)$_q$—NRR' with q being an integer from 1 to 6 inclusive, the values of q being independent of each other between the different groups R₁, R₂ and R₃, and R and R' represent, independently of each other, a hydrogen atom or a group of formula (II):

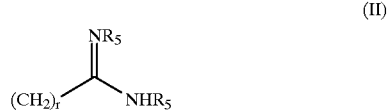

(II)

in which r is an integer which may vary from 0 to 6 inclusive, and the R₅ groups represent, independently of each other, a hydrogen atom or a hydrocarbon residue, it being understood that at least one of the groups R₁, R₂ and R₃ contains at least one group of formula (II), m and n reptesent, independently of each other, an integer which may vary from 1 to 6 inclusive with, when n is greater than 1, m being capable of having different values and R₃ different meanings within the general formula (I), p represents an integer which may vary from 1 to 6 inclusive, and R₄ represents a group of general formula (III):

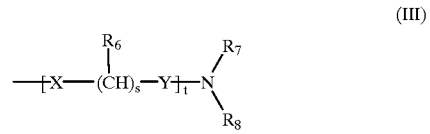

(III)

in which:
R₇ and R₈ represent, independently of each other, a hydrogen atom or a lipophilic group, at least one of the groups R₇ and R₈ being different from hydrogen, t is an integer chosen from 0 to 10 inclusive with R₆, X, Y and s being capable of having different meanings within the different units [X—(CHR₆)$_s$—Y] when t is an integer greater than 1, X represents an oxygen or sulphur atom or an amino or alkylamino group, the alkyl substituent being linear or branched and containing 1 to 8 carbon atoms, Y represents a carbonyl group or a methylene group, R₆ represents a hydrogen atom or a natural amino acid side chain, substituted where appropriate and s represents an integer varying between 1 and 10 inclusive with, when s is equal to 1, R₆ representing a natural amino acid side chain, substituted where appropriate, and when s is greater than 1, R₆ representing a hydrogen atom.

The term "DL form" as used above means a mixture of D and L forms in any proportion, and for example in equal proportions.

For the purposes of the invention, "hydrocarbon residue" is understood to mean any aliphatic or aromatic alkyl, carbamate or acyl substituent which is optionally halogenated. Among the aliphatic residues, there may be mentioned more particularly cyclic or noncyclic, linear or branched, saturated or unsaturated aliphatic residues which are optionally halogenated. More preferably, it is an aliphatic residue containing 1 to 10 carbon atoms. In particular, it represents alkanoyl, alkyl, and alkylcarbamate substituents such as, for example, formyl, butyl, tert-butyl or tert-butylcarbamate substituents. According to a variant of the invention, R₅ represents tert-butylcarbamate.

Among the aromatic residues, there may be mentioned more particularly benzyl and its substituted derivatives such as chlorobenzyl, benzylcarbamate or chlorobenzylcarbamate.

Preferably, $R_5$ represents tert-butylcarbamate, benzylcarbamate or chlorobenzylcarbamate.

In a first variant of the invention, one of the $R_5$ groups represents a hydrogen atom and the other an aliphatic residue containing 1 to 10 carbon atoms.

In a second variant of the invention, one of the $R_5$ groups represents a hydrogen atom and the other an aromatic residue preferably chosen from benzyl and its derivatives.

In another variant of the invention, the two $R_5$ groups represent hydrogen atoms.

Advantageously, when $R_1$, $R_2$ and/or $R_3$ are different from hydrogen and comprise the general formula (II), q takes the value 2 or 3 and r is equal to 0.

Preferably, in the general formula (I), m is chosen from 2, 3 and 4.

As indicated above, in formula (III), at least one of the groups $R_7$ and $R_8$ represents a lipophilic group. For the purposes of the invention, "lipophilic group" is understood to mean any group of the hydrophobic, lipid type which promotes cellular penetration known to persons skilled in the art. It may represent in particular one or more aliphatic fatty chains, a steroid derivative, a natural or synthetic lipid, preferably capable of forming lamellar or hexagonal phases, or optionally a combination of these. It may represent more particularly a linear or branched, saturated or unsaturated aliphatic radical containing 5 to 22 carbon atoms which is optionally 7 halogenated. It may also represent a steroid derivative or a group $(CH_2)_u$—NH—$R_9$ in which u is an integer between 2 and 6 inclusive and $R_9$ is an acyl radical such as for example cholesteryl formate, arachidonyl or cholic acid.

Other examples of steroid derivatives are in particular cholesterol, cholestanol, 3-α-5-cyclo-5-α-cholestan-6-β-ol, cholic acid, cholesteryl formate, chotestanyl formate, 3α,5-cyclo-5α-cholestan-6β-yl formate, cholesterylamine, 6-(1,5-dimethylhexyl)-3a,5a-dimethylhexadecahydrocyclopenta[a]cyclopropa[2,3]cyclopenta[1,2-f]naphthalen-10-ylamine, or cholestanylamine.

Preferably, the lipophilic group is an aliphatic radical containing between 10 and 22 carbon atoms, preferably 14, 16, 17, 18 or 19 carbon atoms. In particular, the lipophilic groups $(CH_2)_{13}CH_3$, $(CH_2)_{15}CH_3$, $(CH_2)_{16}CH_3$, $(CH_2)_{17}CH_3$, $(CH_2)_{18}CH_3$ and oleyl may be mentioned.

In a specific embodiment, the two groups $R_7$ and $R_8$ represent lipophilic groups as defined above. In particular, in a preferred embodiment, each of the groups $R_7$ and $R_8$ represents an aliphatic chain containing between 5 and 22 carbon atoms, and still more preferably between 12 and 22 carbon atoms.

According to a variant of the invention, $R_6$ represents a side chain of a natural amino acid. In particular, the side chain of a natural amino acid may contain amidinium units such as, for example, the side chain of arginine. This side chain $R_6$ may also, as stated above, be substituted by linear, branched or cyclic, saturated or unsaturated aliphatic groups containing between 1 and 24 carbon atoms. There may be mentioned, by way of example, the amino acid side chains substituted by cholesteryl, arachidonyl or retinoyl radicals, mono- or polyaromatic groups such as, for example, benzyloxycarbonyl, benzyl ester, rhodaminyl or biotinyl derivatives, substituted or otherwise.

In a particularly advantageous embodiment, the claimed compounds comprise, in addition, a targeting component which makes it possible to orient the transfer of the nucleic acid with which they are associated. This targeting component is preferably incorporated, on the compound of general formula (I), at the level of the amino acid side chain represented by the substituent $R_6$. More preferably, the targeting component is linked, covalently or noncovalently, to the compound according to the invention.

It may be an extracellular targeting component which makes it possible to orient the transfer of the nucleic acid towards certain cell types or certain desired tissues (tumour cells, hepatic cells, haematopoietic cells and the like). In this regard, it may be a ligand for a cellular receptor present at the surface of the targeted cell type such as, for example, a sugar, a folate, a transferrin, an insulin, an asialoorosomucoid protein or any bioactive molecule recognized by extracellular receptors. It may also be an intracellullar targeting component which makes it possible to orient the transfer of the nucleic acid towards certain preferential cellular compartments (mitochondria, nucleus and the like) such as, for example, a nuclear localization signal (nls) sequence which promotes accumulation of the transfected DNA inside the nucleus.

More generally, the targeting components which may be used within the framework of the invention include sugars, peptides, oligonucleotides, steroids or lipids. Preferably, they are sugars and/or peptides such as antibodies or antibody fragments, ligands for cell receptors or fragments thereof, receptors or fragments of receptors, and the like. In particular, they may be ligands for receptors for growth factors, receptors for cytokines, receptors for cellular lectins or receptors for adhesion proteins such as integrins. There may also be mentioned the receptor for transferrin, HDL lipids and LDLs. The targeting component may also be a sugar which makes it possible to target lectins such as the asialoglycoprotein receptors or an antibody Fab fragment which makes it possible to target the receptor for the immunoglobulin Fc fragment.

Likewise, it is possible to envisage combining a compound of general formula (I) with a marker of the biotin, rhodamine or folate type for example on the $R_6$ amino acid side chain. This marker may also be a linear or cyclic peptide or pseudopeptide sequence containing the Arg-Gly-Asp epitope for recognizing primary and/or secondary receptors for adhesion proteins of the integrin type.

A specific family of compounds according to the invention is that for which $R_1$ comprises a group of formula (II) and $R_2$ and $R_3$ are hydrogen atoms.

A second specific family of compounds according to the invention is that for which $R_1$ and $R_2$ each comprise a group of formula (II) and $R_3$ is a hydrogen atom.

Another specific family of compounds according to the invention is that for which $R_1$ and $R_3$ each comprise a group of formula (II) and $R_2$ is a hydrogen atom.

Another specific family of compounds according to the invention is that in which $R_1$, $R_2$ and $R_3$ each comprise a group of formula (II).

The new compounds of general formula (I) according to the invention can be provided in the form of preferably nontoxic and pharmaceutically acceptable salts. These nontoxic salts comprise the salts formed with inorganic acids- (hydrochloric, sulphuric, hydrobromic, phosphoric or nitric acid), formed with organic acids (acetic, propionic, succinic, maleic, hydroxymaleic, benzoic, fumaric, methanesulphonic or oxalic acid) or formed with inorganic bases (sodium hydroxide, potassium hydroxide, lithium hydroxide, calcium hydroxide) or organic bases (tertiary amines such as triethylamine, piperidine, benzylamine).

As a representative, there may be mentioned more particularly the compounds according to the invention defined by the general subformulae below:
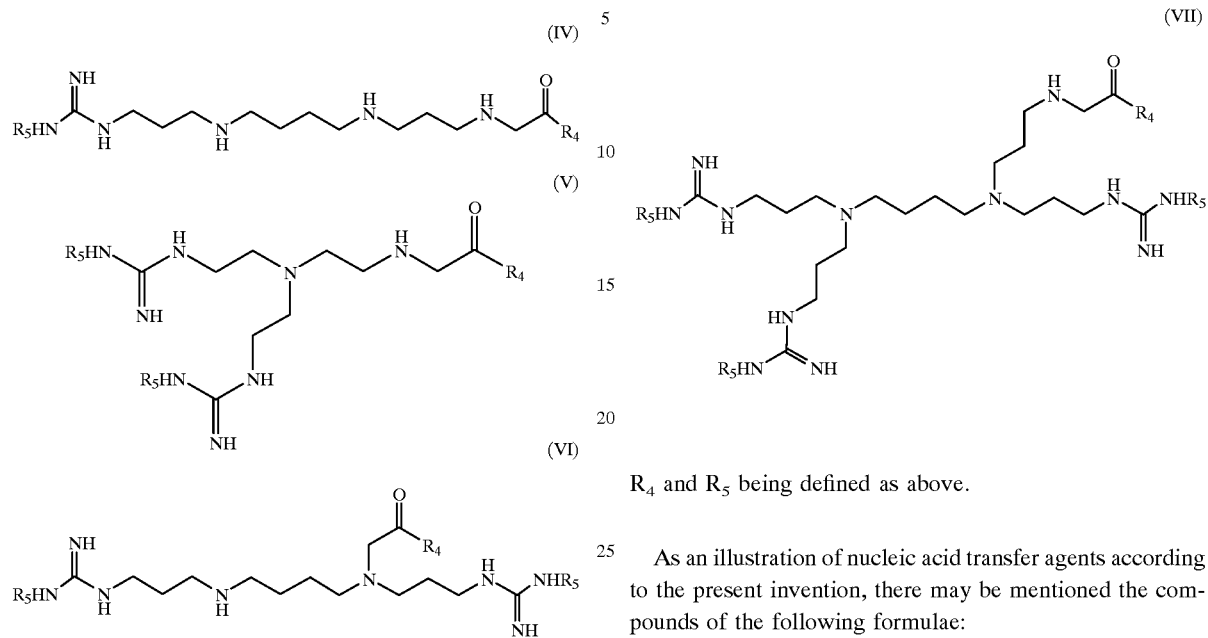
$R_4$ and $R_5$ being defined as above.
As an illustration of nucleic acid transfer agents according to the present invention, there may be mentioned the compounds of the following formulae:
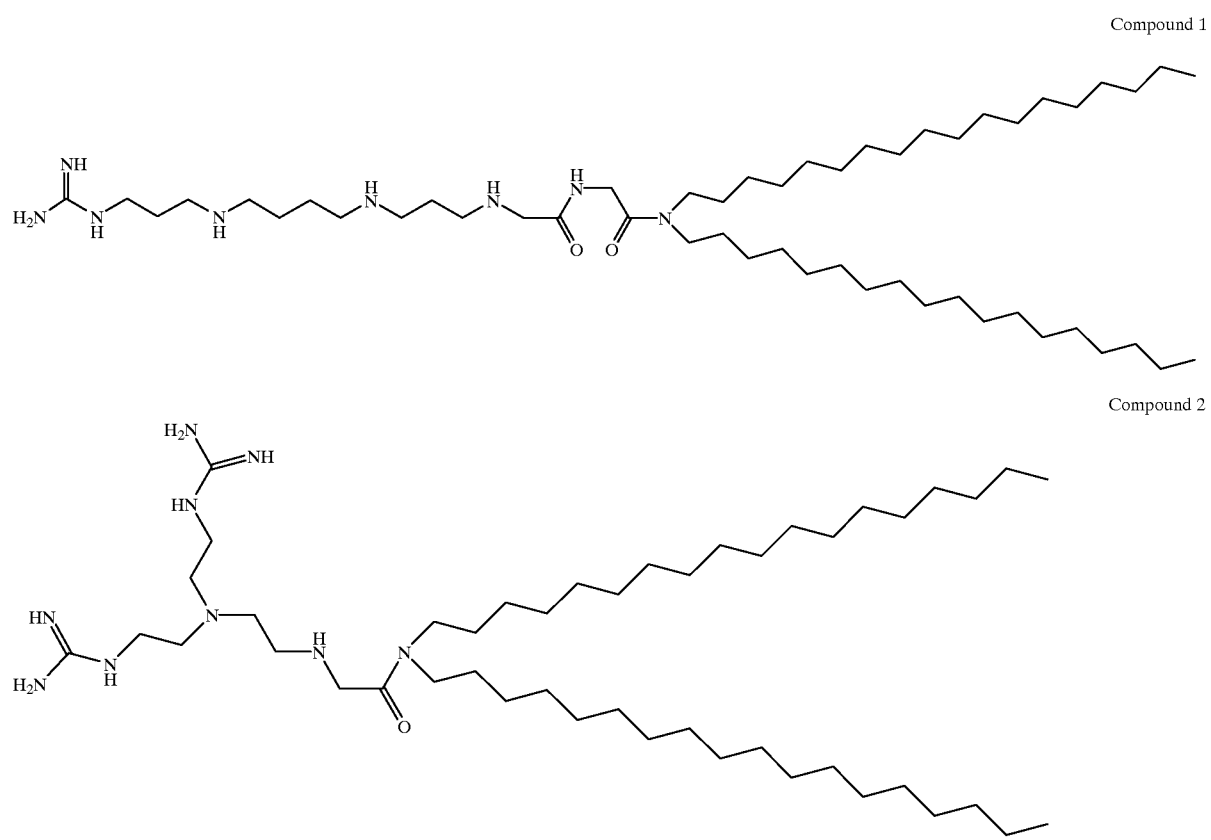

Compound 3
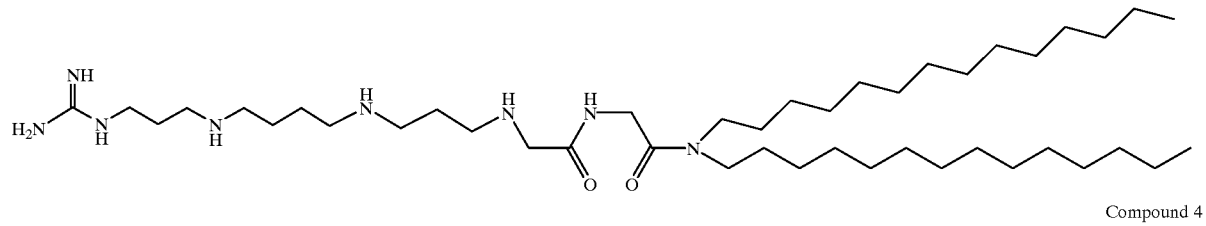

Compound 4
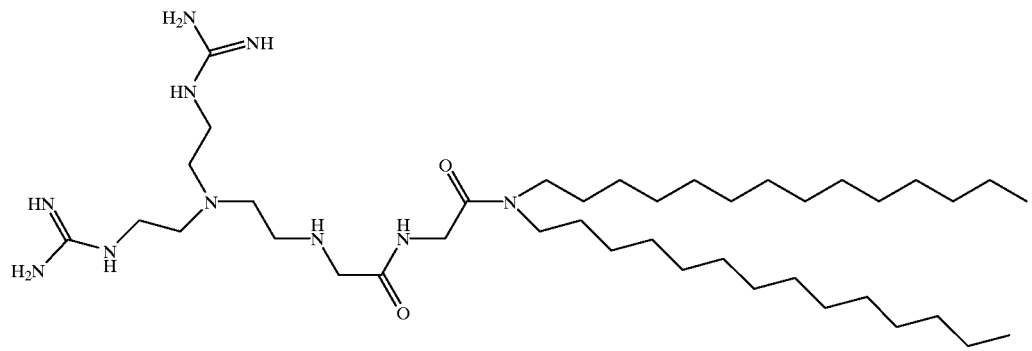

Compound 5
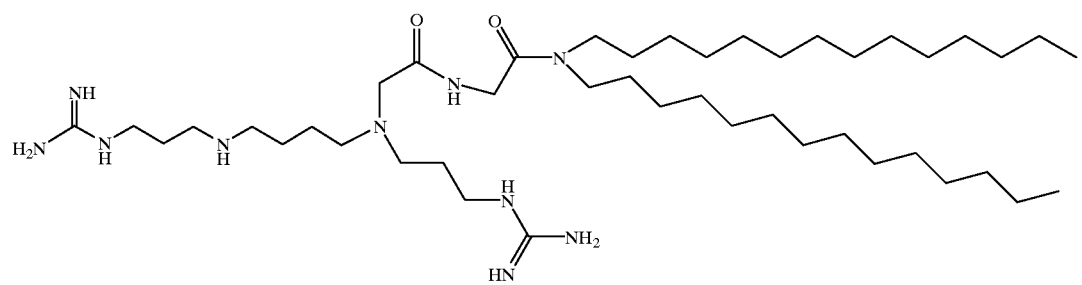

Compound 6
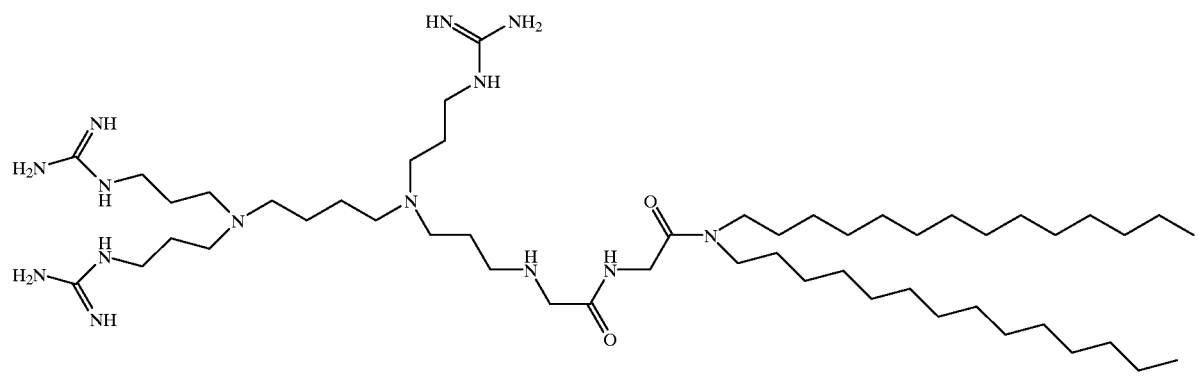

The compounds of the invention may be prepared in various ways, in particular by synthesis in solution and/or by solid phase synthesis on a polymeric support.

According to a first route of synthesis, the compounds of the invention of general formula (I) may be obtained by reacting a thio or oxo derivative of urea, whose amines are optionally protected, with a lipopolyamine of formula (VIII):

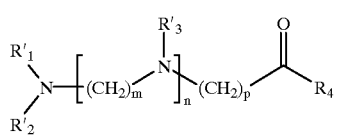
(VIII)

in which $R'_1$, $R'_2$, $R'_3$ represent, independently of each other, a hydrogen atom or a group $(CH_2)_q$—$NR_9R_{10}$, it being possible for q to vary between 1 and 6 inclusive, the different types of q being independent of each other, $R_9$ and $R_{10}$ represent, independently of each other, a hydrogen atom or a group of formula $(CH_2)_r$—$NH_2$, it being possible for r to vary, independently of each other, between 1 and 6 inclusive, and m, n, p and $R_4$ are defined as above.

The action of the urea derivative is in general carried out in the presence of a base, in a suitable protic or aprotic solvent, and at a temperature of between 0° C. and 100° C.

The base used is in general a nonnucleophilic base such as, for example, tertiary amines, sodium carbonate or sodium bicarbonate. Advantageously, tertiary amines, for example triethylamine (TEA) or N-ethyldiisopropylamine (DIEA), are used.

The reaction is advantageously carried out in solvents such as water, alcohols (methanol, ethanol, isopropanol and the like), dimethylformamide, dichloromethane, chloroform, toluene, carbon tetrachloride, benzene, acetonitrile, N-methylpyrrolidone and the like. Preferably, the reaction temperature is between 20° C. and 60° C., and still more preferably between 30° C. and 50° C.

Urea derivatives which are most particularly advantageous are for example O-methylisourea (J. Med. Chem., 38(1995) 16, 3053–3061), S-methylisothiourea hemisulphate (Int. J. Pept. Prot. Res., 40(1992), 119–126), bis-Boc-thiourea (Tet. Lett. 48(1993), 7677–7680), N,N'-bis (benzyloxycarbonyl)-S-methylisothiourea or N,N'-bis(tert-butoxycarbonyl)-S-methylisothiourea (Synth. Commun., 26(1996), 2, 407–413).

The lipopolyamines of general formula (VIII) are obtained according to the methods described in Patent Application WO97/18185 incorporated into the present application by way of reference, or by any similar method known to persons skilled in the art.

According to the invention, the transfer agents of general formula (I) may also be obtained by peptide coupling between the acid of general formula (IX);

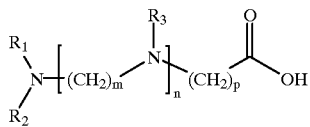

(IX)

and the lipid molecule $R_4H$ for which $R_1$, $R_2$, $R_3$, m, n, p and $R_4$ are defined as above.

The peptide coupling is carried out according to conventional methods (Bodanski M., *Principles and Practices of Peptides Synthesis*, Ed. Springe-Verlag) or by any similar method known to persons skilled in the art.

In particular, the reaction is generally carried out in the presence of a nonnucleophilic base in suitable aprotic solvents, at a temperature of between 0 and 100° C., the pH being adjusted to between 9 and 11.

By way of example, chloroform, dimethylformamide, N-methylpyrrolidone, acetonitrile, dichloromethane, toluene or benzene may be used as solvent.

The nonnucleophilic bases used are preferably tertiary amines, calcium carbonate or sodium bicarbonate. Still more preferably, the bases used are tertiary amines, for example triethylamine (TEA) or N-ethyldiisopropylamine (DIEA).

Advantageously, the reaction is carried out at a temperature of between 0° C. and 50° C., and more preferably between 10° C. and 30° C.

The lipid molecule of formula $R_4H$, for which $R_4$ is defined as above, may be obtained by peptide coupling between the commercially available compound of general formula (X):

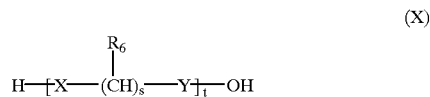

(X)

and the amine of formula $NHR_7R_8$,
for which X, Y, s, t, $R_6$, $R_7$ and $R_8$ are defined as above.

The peptide coupling is carried out according to conventional methods (Bodanski M., *Principles and Practices of Peptides Synthesis*, Ed. Springe-Verlag) or by any similar method known to persons skilled in the art.

In particular, the reaction is generally carried out in the presence of a nonnucleophilic base in suitable aprotic solvents, at a temperature of between 0 and 100° C., the pH being adjusted to between 9 and 11, as described above.

The acid of general formula (IX) may be obtained according to a 3-step solid phase synthesis route as follows:
a polyamine of general formula (XI):

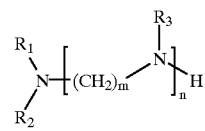

(XI)

for which $R'_1$, $R'_2$, $R'_3$, m and n are defined as above, is grafted on a polymeric support ▣ so as to obtain the grafted compound of general formula (XII):

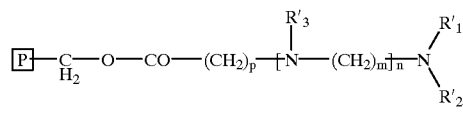

(XII)

The reaction is preferably carried out at a temperature of between 0° C. and 100° C. in the presence of a suitable aprotic solvent, for example chloroform, dichloromethane, dimethylformamide, N-methylpyrrolidone, acetonitrile, toluene, benzene and the like. Advantageously, the reaction temperature is room temperature.

Various polymeric supports are suitable. The commercially available resins are advantageously chosen for the solid phase peptide synthesis (Merrifield synthesis). In particular, the O-chlorotrityl chloride resin or the HMP resin which provide products carrying free acid functions, or a resin of the Rink type may be chosen. The polyamino acids may be synthesized directly on a peptide presynthesized on the solid phase and carrying a bromoalkyl function or a co-aldehyde acid.

The alkylating agents used for the production of the appropriate resin are chosen as a function of the alkylation method. For a conventional alkylation, the bromoacetic acid or the ω-halocarboxylic acids are for example chosen. For a reductive alkylation, a aldehydecarboxylic acid such as glyoxalic acid, succinic semialdehyde and the like, or a keto acid such as acetoacetic acid or pyruvic acid and the like are for example chosen.

The starting polyamines of general formula (XI) are either commercially available, for example spermidine, spermine, tris(2-aminoethyl)amine, phenylenediamine, diaminoethane (propane, butane, pentane, hexane and the like), or may be synthesized by conventional methods, for example by cyanoethylation of commercially available amines such as diaminoethane (propane, butane, pentane, hexane and the like) amine, spermidine, spermine, in order to obtain branched polyamines.

in a second step, the grafted compound of general formula (XII) is reacted with a thio or oxo derivative of urea, in which the amines are optionally protected, in order to obtain a grafted polyaminoamidine compound of general formula (XIII):

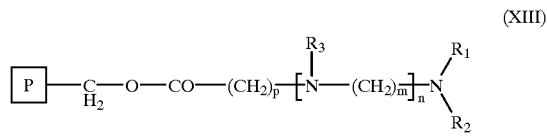

(XIII)

in which $R_1$, $R_2$, $R_3$, m, n and p are defined as above.

The reaction is carried out according to methods known to persons skilled in the art (Bergeron, R. J. and McManis, Total synthesis of 15-Deoxyspergualin, J. Org. Chem., 1987, 52, 1700–1703) or according to similar methods.

The reaction is normally carried out at a temperature of between −20° C. and 100° C. in the presence of a protic or aprotic solvent.

By way of example, water, alcohols (methanol, ethanol, isopropanol and the like), dimethylformamide, dichloromethane, chloroform, aromatic solvents (toluene, benzene and the like), carbon tetrachloride, acetonitrile, N-methylpyrrolidone and the like are used as solvent.

More particularly advantageous derivatives of urea are for example O-methylisourea (J. Med. Chem., 38(1995) 16, 3053–3061), S-methylisothiourea hemisulphate (Int. J. Pept. Prot. Res., 40(1992), 119–126), bis-Boc-thiourea (Tet. Lett. 48(1993), 7677–7680), N,N'-bis(benzyloxycarbonyl)-S-methylisothiourea or N,N'-bis(tert-butoxycarbonyl)-S-methylisothiourea (Synth. Commun., 26(1996), 2, 407–413).

Finally, in a last step, the grafted polyaminoamidines of general formula (XIII) are cleaved from the polymeric support in order to give the acid of general formula (IX) as defined above. The cleavage is carried out according to conventional methods known to persons skilled in the art. In particular, the procedure is carried out by the action. of a weak acid which does not degrade the rest of the molecule. Preferred weak acids are for example fluorinated alcohols, and more particularly 1,1,1-trifluoroethan-2-ol.

Given that the polyaminoamidine of general formula (XIII) contains acid, amino, alkylamino and/or amidine functions, it is preferable, where appropriate, to protect them prior to the cleavage from the polymeric support. The protection may be achieved by any compatible group whose use and removal does not alter the rest of the molecule. In particular, the procedure is carried out according to the methods described in T. W. GREENE, *Protective Groups in Organic Synthesis*, A. Wiley-Interscience Publication (1981), or in McOmie, *Protective Groups in Organic Chemistry*, Plenum Press (1973).

The removal, where appropriate, of the protecting radicals is carried out prior to the peptide coupling between the acid of general formula (IX) obtained after cleavage from the polymeric support, and the compound of formula $R_4H$ according to the usual methods known to persons skilled in the art.

By way of example, the protecting groups may be chosen from the trimethylsilyl, benzhydryl, tetrahydropyranyl, formyl, acetyl, chloracetyl, trichloroacetyl, trifluoroacetyl, ethoxycarbonyl, tert-butoxycarbonyl, trichloroethoxycarbonyl, benzyloxycarbonyl and fluorenyloxycarbonyl radicals and the like.

Any other method known to persons skilled in the art, and in particular those described in Bodanski M., *Principles and Practices of Peptides Synthesis*, Ed. Springe-Verlag, leading to the nucleic acid transfer agents according to the present invention also fall within the scope of the invention.

Another subject of the invention relates to a composition comprising an agent as defined above, and a nucleic acid. Preferably, the compound and the nucleic acid are present in quantities such that the ratio R of the positive charges of the compound to the negative charges of the nucleic acid is between 0.1 and 50, and more preferably between 0.1 and 20. This ratio can be easily adjusted by persons skilled in the art depending on the compound used, the nucleic acid and the desired applications (in particular the type of cells to be transfected).

For the purposes of the invention, "nucleic acid" is understood to mean both a deoxyribonucleic acid and a ribonucleic acid. They may be natural or artificial sequences, and in particular genomic DNA (gDNA), complementary DNA (cDNA), messenger RNA (mRNA), transfer RNA (tRNA), ribosomal RNA (rRNA), hybrid sequences or synthetic or semisynthetic sequences, oligonucleotides which are modified or otherwise. These nucleic acids may be of human, animal, plant, bacterial or viral origin and the like. They may be obtained by any technique known to persons skilled in the art, and in particular by the screening of libraries, by chemical synthesis or by mixed methods including the chemical or enzymatic modification of sequences obtained by the screening of libraries. They may be chemically modified.

As regards more particularly deoxyribonucleic acids, they may be single- or double-stranded, as well as short oligonucleotides or longer sequences. In particular, the nucleic acids advantageously consist of plasmids, vectors, episomes, expression cassettes and the like. These deoxyribonucleic acids may carry a replication origin which is functional or otherwise in the target cell, one or more marker genes, sequences for regulating transcription or replication, genes of therapeutic interest, anti-sense sequences which are modified or otherwise, regions for binding to other cellular components, and the like.

Preferably, the nucleic acid comprises an expression cassette consisting of one or more genes of therapeutic interest under the control of one or more promoters and of a transcriptional terminator which is active in the target cells.

For the purposes of the invention, gene of therapeutic interest is understood to mean in particular any gene encoding a protein product having a therapeutic effect. The protein product thus encoded may be in particular a protein or a peptide. This protein product may be exogenous, homologous or endogenous with respect to the target cell, that is to say a product which is normally expressed in the target cell when the latter exhibits no pathology. In this case, the expression of a protein makes it possible, for example, to overcome an insufficient expression in the cell or the expression of a protein which is inactive or weakly active because of a modification, or to overexpress the said protein. The gene of therapeutic interest may also encode a mutant of a cellular protein, having an increased stability, a modified activity and the like. The protein product may also be heterologous with respect to the target cell. In this case, an expressed protein may, for example, complement or provide an activity which is deficient in the cell, allowing it to combat a pathology, or to stimulate an immune response.

Among the therapeutic products for the purposes of the present invention, there may be mentioned more particularly enzymes, blood derivatives, hormones, lymphokines, interleukins, interferons, TNF and the like (FR 92/03120), growth factors, neurotransmitters or their precursors or synthesis enzymes, trophic factors (BDNF, CNTF, NGF, IGF, GMF, aFGF, bFGF, NT3, NT5, HARP/pleiotrophin, and the like), apolipoproteins (ApoAI, ApoAIV, ApoE, and the like, FR 93/05125), dystrophin or a minidystrophin (FR 91/11947), the CFTR protein associated with cystic fibrosis, tumour suppressor genes (p53, Rb, Rap1A; DCC; k-rev, and the like, FR 93/04745), genes encoding factors involved in coagulation (factors VII, VIII, IX), genes involved in DNA repair, suicide genes (thymidine kinase, cytosine deaminase), genes for haemoglobin or other proteinaceous transporters, metabolic or catabolic enzymes and the like.

The nucleic acid of therapeutic interest may also be an anti-sense gene or sequence, whose expression in the target cell makes it possible to control the expression of genes or the transcription of cellular mRNAs. Such sequences may, for example, be transcribed in the target cell into RNA complementary to cellular mRNAs and thus block their translation into protein, according to the technique described in Patent EP 140,308. The therapeutic genes also comprise sequences encoding ribozymes, which are capable of selectively destroying target RNAs (EP 321,201).

The nucleic acid may also contain one or more genes encoding an antigenic peptide, capable of generating an immune response in humans or animals. In this particular embodiment, the invention allows the production either of vaccines or of immunotherapeutic treatments applied to humans or to animals, in particular against microorganisms, viruses or cancers. This may include in particular antigenic peptides specific for the Epstein Barr virus, the HIV virus, the hepatitis B virus (EP 185,573), the pseudorabies virus, the "syncitia forming virus", other viruses or antigenic peptides specific for tumours (EP 259,212).

Preferably, the nucleic acid also comprises sequences allowing the expression of the gene of therapeutic interest and/or of the gene encoding the antigenic peptide in the desired cell or organ. They may be sequences which are naturally responsible for the expression of the gene considered when these sequences are capable of functioning in the infected cell. They may also be sequences of a different origin (responsible for the expression of other proteins, or even synthetic). In particular, they may be promoter sequences of eukaryotic or viral genes. For example, they may be promoter-sequences derived from the genome of the cell which it is desired to infect. Likewise, they may be promoter sequences derived from the genome of a virus. In this regard, there may be mentioned, for example, the promoters of the E1A, MLP, CMV and RSV genes and the like. In addition, these expression sequences may be modified by the addition of activating and regulatory sequences and the like. They may also include an inducible or repressible promoter.

Moreover, the nucleic acid may also contain, in particular upstream of the gene of therapeutic interest, a signal sequence directing the therapeutic product synthesized in the secretory pathways of the target cell. This signal sequence may be the natural signal sequence of the therapeutic product, but it may also be any other functional signal sequence, or an artificial signal sequence. The nucleic acid may also contain a signal sequence directing the synthesized therapeutic product towards a particular cellular compartment.

In another embodiment, the present invention also relates to compositions comprising a nucleic acid, a transfection agent (I) as defined above and one or more adjuvants capable of combining with the transfection agent/nucleic acid complex and of improving its transfecting power. The presence of this type of adjuvant (lipids, peptides or proteins for example) can advantageously make it possible to increase the transfecting power of the compounds.

In this regard, the compositions of the invention may comprise, as adjuvant, one or more neutral lipids. Such compositions are particularly advantageous, in particular when the charge ratio R of nucleolipid complexes is low. The applicant has indeed shown that the addition of a neutral lipid makes it possible to improve the formation of the nucleolipid particles and to promote the penetration of the particle into the cell by destabilizing its membrane.

More preferably, the neutral lipids used within the framework of the present invention are lipids containing 2 fatty chains. In a particularly advantageous manner, natural or synthetic lipids which are zwitterionic or lacking ionic charge under physiological conditions are used. They may be chosen more particularly from dioleoylphosphatidylethanolamine (DOPE), oleoylpalmitoylphosphatidylethanolamine (POPE), di-stearoyl, -palmitoyl and -myristoylphosphatidylethanolamines as well as their derivatives which are N-methylated 1 to 3 times; phosphatidyl glycerols, diacylglycerols, glycosyldiacylglycerols, cerebrosides (such as in particular galactocerebrosides), sphingolipids (such as for example sphingomyelins), or asialogangliosides (such as in particular asialoGM1 and GM2).

These different lipids may be obtained either by synthesis or by extraction from organs (for example the brain) or from eggs, by conventional techniques well known to persons skilled in the art. In particular, the extraction of the natural lipids may be carried out by means of organic solvents (see also Lehninger, Biochemistry).

More recently, the Applicant has demonstrated that it was also particularly advantageous to use, as adjuvant, a compound directly involved or otherwise in the condensation of the said nucleic acid (WO 96/25508). The presence of such a compound in a composition according to the invention makes it possible to reduce the quantity of transfecting compound, with the beneficial consequences resulting therefrom from the toxicological point of view, without any damaging effect on the transfecting activity. Compound involved in the condensation of the nucleic acid is intended to define a compound which compacts, directly or otherwise, the nucleic acid. More precisely, this compound may either act directly at the level of the nucleic acid to be transfected, or may be involved at the level of an additional compound which is directly involved in the condensation of this nucleic acid. Preferably, it acts directly at the level of the nucleic acid. For example, the precompacting agent may be any polycation, and for example polylysine. According to a preferred embodiment, this agent which is involved in the condensation of the nucleic acid is derived, as a whole or in part, from a protamine, from a histone, or from a nucleolin and/or from one of their derivatives. Such an agent may also consist, as a whole or in part, of peptide units (KTPKKAKKP) (SEQ ID NO:1) and/or (ATPAKKAA) (SEQ ID NO:2), it being possible for the number of units to vary between 2 and 10. In the structure of the compound according to the invention, these units may be repeated continuously or otherwise. They may thus be separated by linkages of a biochemical nature, for example by one or more amino acids, or of a chemical nature.

Preferably, the compositions of the invention comprise from 0.01 to 20 equivalents of adjuvant per equivalent of nucleic acids in mol/mol, and more preferably from 0.5 to 5.

In a particularly advantageous embodiment, the compositions of the present invention comprise, in addition, a targeting component which makes it possible to orient the transfer of the nucleic acid. This targeting component may be a component for extracellular targeting which makes it possible to orient the transfer of the DNA towards certain cell types or certain tissues desired (tumour cells, hepatic cells, haematopoietic cells and the like). It may also be an intracellular targeting component which makes it possible to orient the transfer of the nucleic acid towards certain preferred cell compartments (mitochondria, nucleus and the like). The targeting component may be linked to the nucleic acid transfer agent according to the invention or also to the nucleic acid as specified above.

Among the targeting components which can be used within the framework of the invention, there may be mentioned sugars, peptides, proteins, oligonucleotides, lipids, neuromediators, hormones, vitamins or their derivatives. Preferably, they are sugars, peptides or proteins such as antibodies or antibody fragments, ligands for cellular receptors or fragments thereof, receptors or receptor fragments and the like. In particular, they may be ligands for growth factor receptors, cytokine receptors, receptors of the cellular lectin type, or ligands containing an RGD sequence with an affinity for the receptors for adhesion proteins such as integrins. There may also be mentioned the receptors for transferrin, HDLs and LDLs, or the folate transporter. The targeting component may also be a sugar which makes it possible to target lectins such as the receptors for the asialoglycoproteins or syalydes such as the sialyde Lewis X or an antibody Fab fragment, or a single-chain antibody (ScFv).

The combination of the targeting components with the nucleolipid complexes may be carried out by any technique known to persons skilled in the art, for example by coupling to a hydrophobic portion or to a portion which interacts with the nucleic acid of the transfer agent according to the invention, or to a group which interacts with the transfer agent according to the invention or with the nucleic acid. The interactions in question may be, according to a preferred mode, of an ionic or covalent nature.

The subject of the invention is also the use of the compounds as defined above for the transfer of nucleic acids (and more generally of polyanions) into cells.

For uses in vivo, for example for studying the regulation of genes, the creation of animal models of pathological conditions, or in therapy, the compositions according to the invention can be formulated for administration by the topical, cutaneous, oral, rectal, vaginal, parenteral, intranasal, intravenous, intramuscular, subcutaneous, intraocular, transdennal, intratracheal or intraperitoneal route, and the like. Preferably, the compositions of the invention contain a vehicle which is pharmaceutically acceptable for an injectable formulation, in particular for a direct injection into the desired organ, or for administration by the topical route (on the skin and/or the mucous membrane). They may be in particular isotonic sterile solutions, or dry, in particular freeze-dried, compositions which, upon addition, depending on the case, of sterilized water or of physiological saline, allow the constitution of injectable solutions. The nucleic acid doses used for the injection as well as the number of administrations may be adapted according to various parameters, and in particular according to the mode of administration used, the relevant pathological condition, the gene to be expressed, or the desired duration of treatment. As regards more particularly the mode of administration, it may be either a direct injection into the tissues, for example at the level of the tumours, or the circulatory system, or a treatment of cells in culture followed by their reimplantation in vivo, by injection or transplantation. The relevant tissues or circulatory system within the framework of the present invention are for the example the muscles, the skin, the brain, the lungs, the liver, the spleen, the bone marrow, the thymus, the heart, the lymph, the blood, the bones, the cartilage, the pancreas, the kidneys, the bladder, the stomach, the intestines, the testicles, the ovaries, the rectum, the nervous system, the eyes, the glands, the connective tissues and the like.

The invention relates, in addition, to a method of transferring nucleic acids into cells comprising the following steps:

(1) bringing the nucleic acid into contact with a transfer agent as defined above, to form a complex, and (2) bringing the cells into contact with the complex formed in (1).

The cells may be brought into contact with the complex by incubating the cells with the said complex (for uses in vitro or ex vivo), or by injecting the complex into an organism (for uses in vivo). The incubation is preferably carried out in the presence, for example, of 0.01 to 1000 $\mu$g of nucleic acid per $10^6$ cells. For in vivo administration, nucleic acid doses of between 0.01 and 10 mg can, for example, be used.

In the case where the compositions according to the present invention contain, in addition, one or more adjuvants and/or a targeting component as defined above, the adjuvant (s) and/or the targeting component are mixed beforehand with the transfer agent according to the invention or with the nucleic acid.

The present invention thus provides a particularly advantageous method for the transfer of nucleic acids, in particular for the treatment of diseases, comprising the in vitro, in vivo or ex vivo administration of a nucleic acid capable of correcting the said disease, combined with a transfer agent of general formula (I) under the conditions defined above. More particularly, this method is applicable to diseases resulting from a deficiency in a protein or nucleic product, the administered nucleic acid encoding the said protein product or being transcribed into a nucleic product, or constituting the said nucleic product.

The present invention also extends to any use of a transfer agent of general formula (I) according to the invention for the in vivo, ex vivo or in vitro transfection of cells.

The compounds of the invention can be used in particular for the transfer of nucleic acids into primary cells or into established lines. They may be fibroblast cells, muscle cells, nerve cells (neurones, astrocytes, glial cells), hepatic cells, cells of the haematopoietic line (lymphocytes, CD34, dendritic cells, and the like), epithelial cells, and the like, in differentiated or pluripotent form (precursors).

In addition to the preceding features, the present invention also comprises other characteristics and advantages which will emerge from the examples and figures which follow, and which should be considered as illustrating the invention without limiting the scope thereof.

FIGURES

FIG. 1: Diagram of the synthesis of compound 1 according to the invention.

Figure 2:
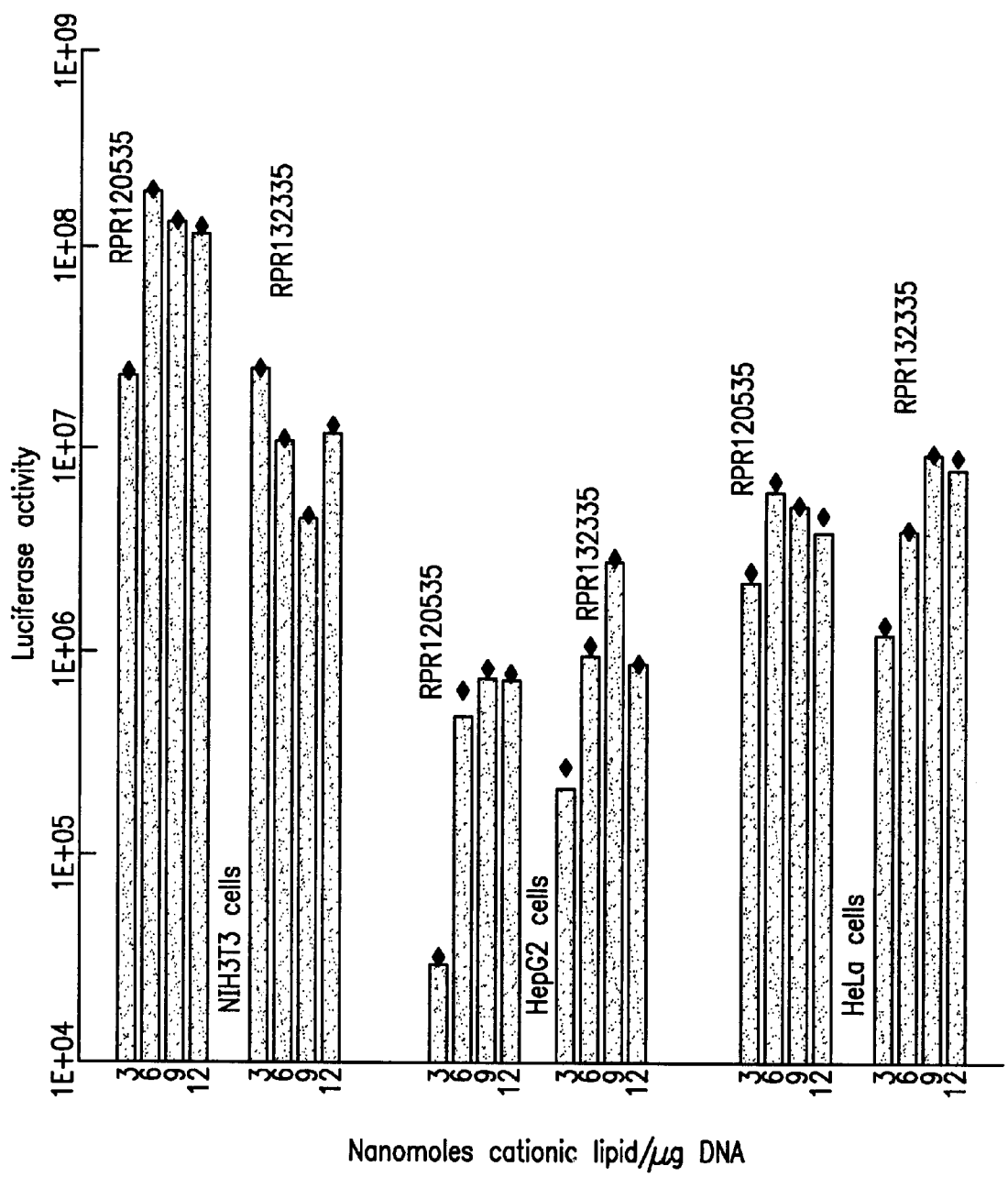

FIG. 2: Measurement of the in vitro efficiency of transfection of compound 1 according to the invention into NIH3T3, HepG2 and HeLa cells, in the absence of serum proteins and in comparison with its amine-containing homologue (RPR120535).

"Amine-containing homologue" is understood to mean the cationic lipid which is identical with the exception of the amidine and/or guanidine functions which are replaced by amino functions.

The measurements were carried out at different charge ratios which are plotted on the x-axis. The expression of luciferase is plotted on the y-axis and is expressed in RLU (Relative Light Unit) per well.

Figure 3:
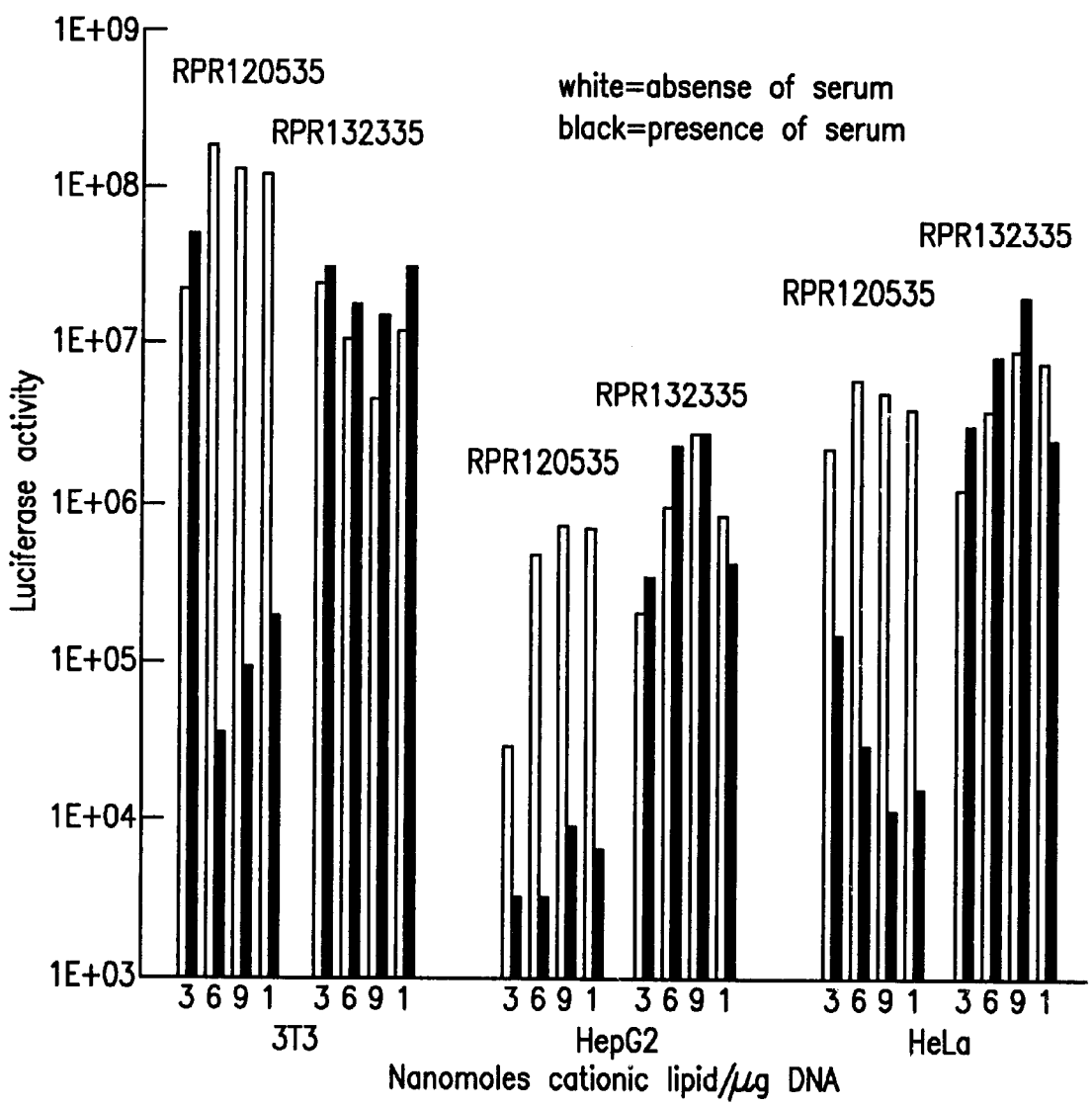

FIG. 3: Measurement of the in vitro efficiency of transfection of compound 1 according to the invention into NIH3T3, HepG2 and HeLa cells, in the absence (white bars) and in the presence (black bars) of serum proteins and in comparison with its amine-containing homologue (RPR120535).

The measurements were carried out at different charge ratios which are plotted on the x-axis. The expression of luciferase is plotted on the y-axis and is expressed in RLU (Relative Light Unit) per well.

Figure 4:
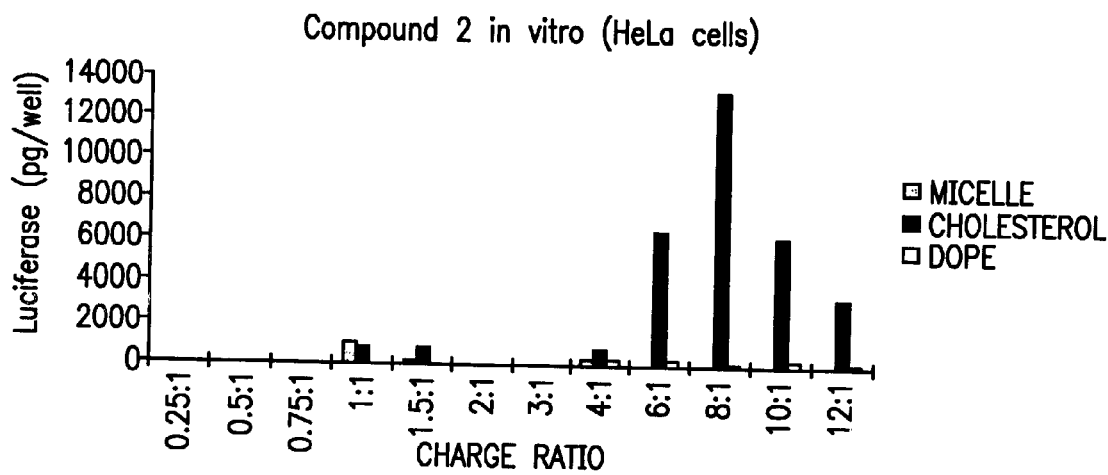

FIG. 4: Measurement of the in vitro efficiency of transfection of compound 2 according to the invention into HeLa cells, in the absence of serum proteins. The measurements were carried out for compound 2 in micellar form and in combination with a neutral colipid (DOPE and cholesterol).

The x-axis represents the charge ratio for the complex formed between the cationic lipid and the DNA. The y-axis represents the expression of luciferase expressed in pg/well, each well containing 100,000 cells.

Figure 5:
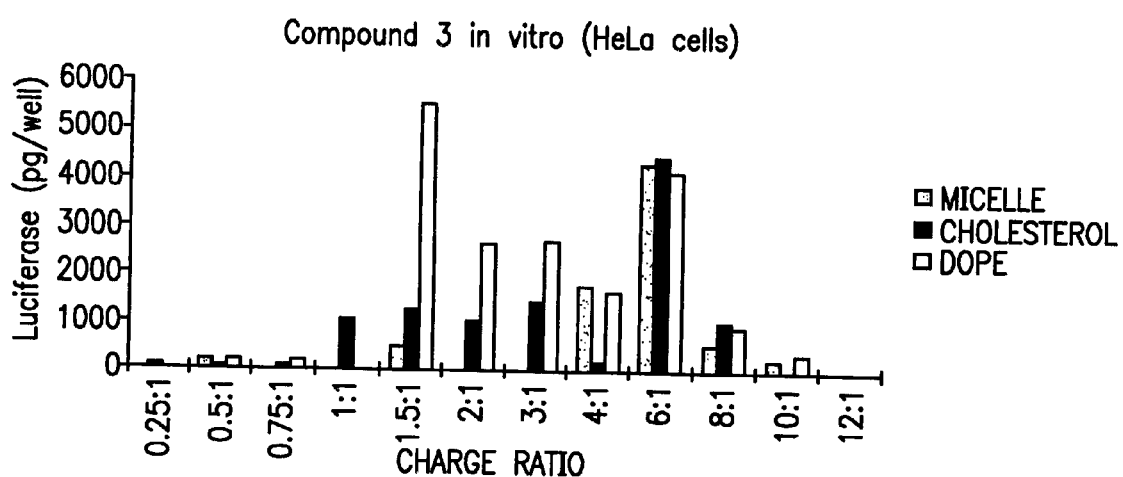

FIG. 5: Measurement of the in vitro efficiency of transfection of compound 3 according to the invention into HeLa cells, in the absence of serum proteins. The measurements were carried out for compound 3 in micellar form and in combination with a neutral colipid (DOPE and cholesterol).

The x-axis represents the charge ratio for the complex formed between the cationic lipid and the DNA. The y-axis represents the expression of luciferase expressed in pg/well, each well containing 100,000 cells.

Figure 6:
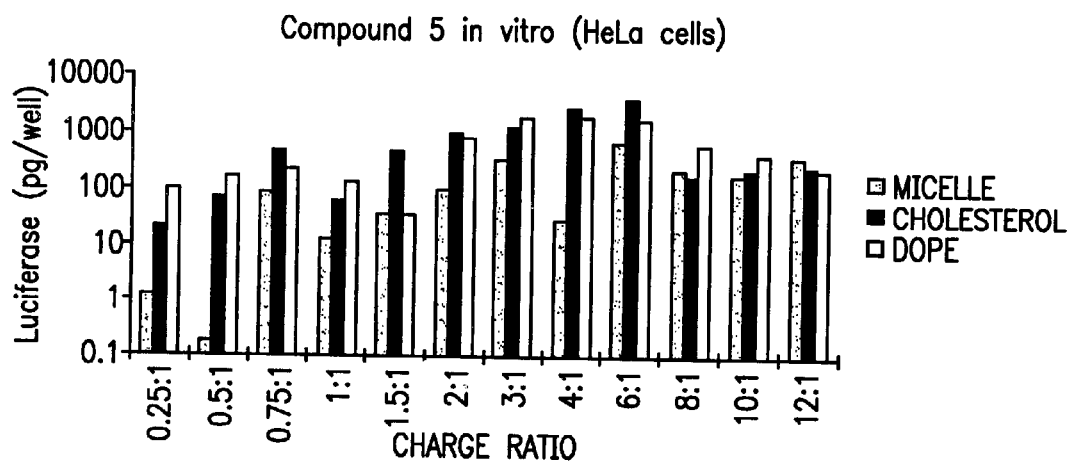

FIG. 6: Measurement of the in vitro efficiency of Lransfection of compound 5 according to the invention into HeLa cells, in the absence of serum proteins. The measurements were carried out for compound 5 in micellar form and in combination with a neutral colipid (DOPE and cholesterol).

The x-axis represents the charge ratio for the complex formed between the cationic lipid and the DNA. The y-axis represents the expression of luciferase expressed in pg/well, each well containing 100,000 cells.

Figure 7:
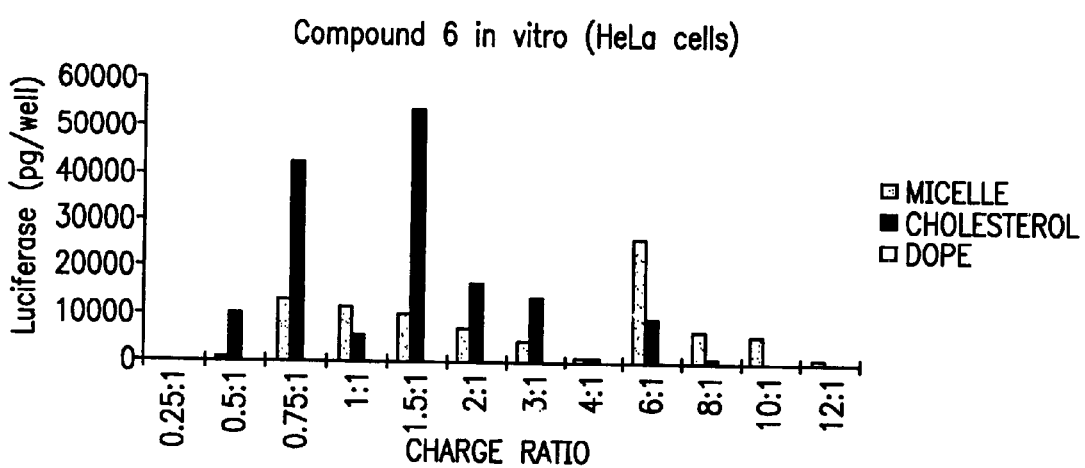

FIG. 7: Measurement of the in vitro efficiency of transfection of compound 6 according to the invention into HeLa cells, in the absence of serum proteins. The measurements were carried out for compound 6 in micellar form and in-combination with a neutral colipid (DOPE and cholesterol).

The x-axis represents the charge ratio for the complex formed between the cationic lipid and the DNA. The y-axis represents the expression of luciferase expressed in pg/well, each well containing 100,000 cells.

FIG. 8: Tables indicating the physicochemical phase (phase A, B or C) in which exist the nucleolipid complexes formed with compound 2 in comparison with its amine-containing analogue, as a function of the charge ratio.

The determination of the phases was carried out for compound 2 and for its amine-containing homologue in micellar form and in combination with a neutral colipid (DOPE and cholesterol).

By comparing the 2 tables, a shift is observed from the unstable phase B towards lower charge ratios in the case of compound 2.

FIG. 9: Tables indicating the physicochemical phase (phase A, B or C) in which exist the nucleolipid complexes formed with compound 3 in comparison with its amine-containing analogue, as a function of the charge ratio.

The determination of the phases was carried out for compound 3 and for its amine-containing homologue in micellar form and in combination with a neutral colipid (DOPE and cholesterol).

By comparing the 2 tables, a shift is observed from the unstable phase B towards lower charge ratios in the case of compound 3.

FIG. 10: Tables indicating the physicochemical phase (phase A, B or C) in which exist the nucleolipid complexes formed with compound 5 in comparison with its amine-containing analogue, as a function of the charge ratio.

The determination of the phases was carried out for compound 5 and for its amine-containing homologue in micellar form and in combination with a neutral colipid (DOPE and cholesterol).

By comparing the 2 tables, a shift is observed from the unstable phase B towards lower charge ratios in the case of compound 5.

FIG. 11: Tables indicating the physicochemical phase (phase A, B or C) in which exist the nucleolipid complexes formed with compound 6 in comparison with its amine-containing analogue, as a function of the charge ratio.

The determination of the phases was carried out for compound 6 and for its amine-containing homologue in micellar form and in combination with a neutral colipid (DOPE and cholesterol).

By comparing the 2 tables, a shift is observed from the nstable phase B towards lower charge ratios in the ase of compound 6.

FIG. 12: Table representing the reduction in fluorescence after addition of ethidium bromide for compounds 2, 3, 5 and 6 in the form of micelles. The replacement of the ethidium bromide of the DNA with the lipid is an indication of binding to the DNA. The fluorescence obtained by the DNA alone is defined as being 100%.

FIG. 13: Table representing the reduction in fluorescence after addition of ethidium bromide for compounds 2, 3, 5 and 6 in the presence of cholesterol. The replacement of the ethidium bromide of the DNA with the lipid is an indication of binding to the DNA. The fluorescence obtained by the DNA alone is defined as being 100%.

FIG. 14: Table representing the reduction in fluorescence after addition of ethidium bromide for compounds 2, 3, 5 and 6 in the presence of DOPE. The replacement of the ethidium bromide of the DNA with the lipid is an indication of binding to the DNA. The fluorescence obtained by the DNA alone is defined as being 100%.

Figure 15:
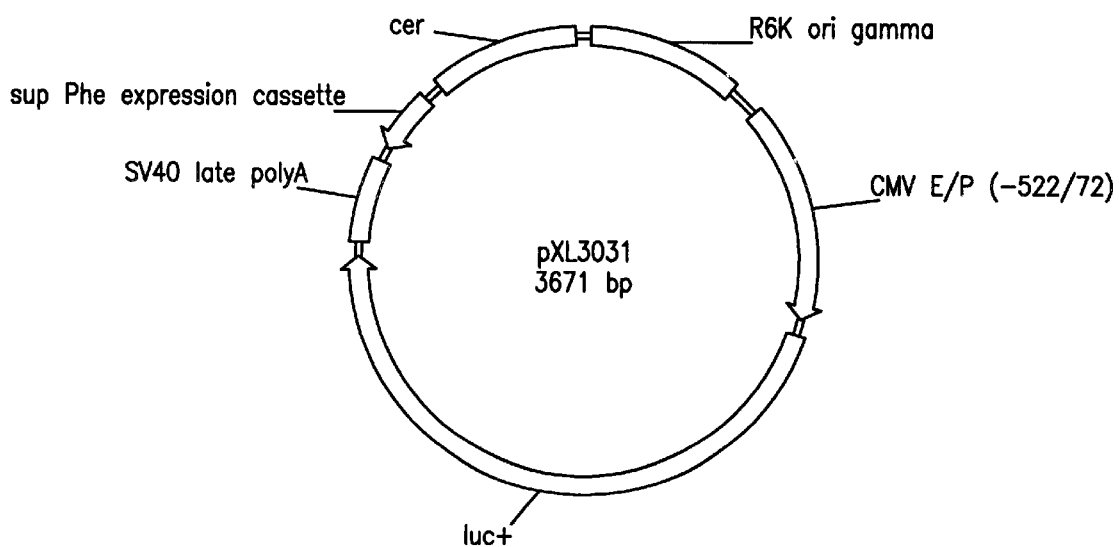

FIG. 15: Representation of the plasmid pXL3031.

| ABBREVIATIONS AND SYMBOLS | |
|---|---|
| AcOEt: | ethyl acetate |
| BOC: | tert-butoxycarbonyl |
| BOP: | benzotriazol-1-yloxytris(dimethylamino)-phosphonium hexafluorophosphate |
| DCC: | dicyclohexylcarbodiimide |
| DCU: | dicyclohexylurea |
| DIEA: | N-ethyldiisopropylamine |
| DMAP: | 4-dimethylaminopyridine |
| DMF: | dimethylformamide |

-continued

ABBREVIATIONS AND SYMBOLS

| | |
|---|---|
| DMSO: | dimethyl sulphoxide |
| DODA: | dioctadecylamine |
| PE: | petroleum ether |
| EtOH: | ethanol |
| $NEt_3$: | triethylamine |
| Rf: | retention factor |
| TEA: | triethylamine |
| TFA: | trifluoroacetic acid |
| THF: | tetrahydrofuran |
| TMS: | tetramethylsilane |
| UV: | ultraviolet radiation |
| SPPS: | solid phase peptide synthesis |
| HPLC: | high-performance liquid chromatography |
| Z: | benzyloxycarbonyl |
| ClZ: | p-chlorobenzyloxycarbonyl |

MATERIALS AND METHODS FOR THE CHEMICAL SYNTHESIS a) Compounds

The starting polyamines are commercially available, for example spermidine, spermine, tris-(2-aminoethyl)amine, phenylenediamine, diaminoethane (propane, butane, pentane, hexane, and the like), or can be synthesized by conventional methods, for example by cyanoethylation of commercially available amines such as diaminoethane (propane, butane, pentane, hexane, and the like), amine, spermidine, spermine, to give branched polyamines.

The polymers used are commercially available resins for solid-phase peptide synthesis (Merrifield synthesis), in particular the resin O-chlorotrityl chloride, the resin HMP, which provide products carrying free acid functional groups or a Rink-type resin. The polyamino acids can be synthesized directly on a peptide presynthesized on the solid phase and carrying a bromoalkyl functional group or a $\omega$-aldehyde acid.

Dioctadecylamine, triethylamine, trifluoroacetic, BOP, DMAP, benzyl chloroformate are commercial products. The NaCl and $NaHCO_3$ solutions are saturated; the $KHSO_4$ solution is 0.5 M.

b) Physical Measurements

The Proton NMR spectra were recorded on Bruker 400 and 600 MHz spectrometers.

The mass spectra (MS) were obtained on an API-MS/III.

c) Purification and Analytical Techniques a) Direct Phase Chromatography Conditions The thin-layer chromatographies (TLC) were carried out on Merck silica gel plates 0.2 mm thick. They are developed either using UV (254 nm), with ninhydrin, by spraying (a light spray) an ethanolic solution of ninhydrin (40 mg/100 ml of EtOH) in order to reveal the amines or the amides by heating to 150° C., with fluorescamine by spraying a solution (40 mg/100 ml acetone) in order to reveal the primary amines, or with iodine by covering the plate with iodine powder.

The direct phase column chromatographies were carried out on a Merck 60 silica gel of particle size 0.063–0.200 mm.

b) Analytical Chromatography Techniques

The HPLC analyses (High-Performance Liquid Chromatography) are performed on a Merck-Hitachi apparatus equipped with a HITACHI D 2500 integrator-calculator, an autosampler AS-2000A, an intelligene Pump L-6200A and a UV-vis detector L-4000 with an adjustable wavelength set at 220 nm for analytical separations. The columns for the analytical separations are BU-300 aquapore Butyl 7m, 300 A 300×4.6 mm columns from Perkin-Elmer. The mobile phases are demineralized water containing 0.1% TFA and acetonitrile containing 0.1% TFA. The injections of a solution of about 1 mg/ml into a 100 $\mu$l loop valve are 20 $\mu$l. The flow rate for the analyses is set at 1 ml/min.

| Separation conditions: | | | |
|---|---|---|---|
| Solvent A | | Solvent B | |
| Demineralized water | 2500 ml | Acetonitrile for HPLC | 2500 ml |
| Trifluoroacetic acid | 2 ml | Trifluoroacetic acid | 2.5 ml |
| Gradient: | | | |
| Time in min | % solvent A | % solvent B | Flow rate in ml/min |
| 0 | 60 | 40 | 1 |
| 3 | 60 | 40 | 1 |
| 20 | 0 | 100 | 1 |
| 35 | 0 | 100 | 1 |
| 35.1 | 60 | 40 | 4 |
| 36.1 | 60 | 40 | 4 |
| 36.2 | 60 | 40 | 2 |
| 44 | 60 | 40 | 2 | c) Preparative Chromatography Techniques

The equipment is a set for liquid-phase chromatography in gradient mode, allowing UV detection. This preparative chain is composed of the following components:

Pump A: GILSON model 305 equipped with a 50 SC head.
Punp B: GILSON model 303 equipped with a 50 SC head.
Injection loop: GILSON model 303 equipped with a 25 SC head.
Pressure module: GILSON model 806.
Mixer: GILSON model 811 C equipped with a 23 ml head.
UV detector: GILSON model 119 equipped with a preparative cell.
Fraction collector: GILSON model 202 equipped with No. 21 racks.
Intergrator: SHIMADZU model C-R6A.
Column: Column C4 (10 mm) made of stainless steel 25 cm long and 2.2 cm in diameter, marketed by VYDAC model 214 TP 1022.

The solution of product to be purified is loaded onto the column by the injection pump at the flow rate of ml/min, and the eluate is recovered in fraction in a tube in 30 seconds. The detector is set at wavelengths of 220 nm and 235 nm.

The mobile phases are defined in the following manner:

| Solvent A | | Solvent B | |
|---|---|---|---|
| Demineralized water | 2500 ml | Acetonitrile for HPLC | 2500 ml |
| Trifluoroacetic acid | 2 ml | Trifluoroacetic acid | 2.5 ml |
| Gradient: | | | |
| Time in min | % solvent A | % solvent B | Flow rate in ml/min |
| 0 | 70 | 30 | 18 |
| 10 | 70 | 30 | 18 |
| 80 | 0 | 100 | 18 |
| 120 | 0 | 100 | 18 | d) Solid Phase Peptide Synthesis Technique (SPPS)

The solid-phase synthesis is carried out in a manual reactor for SPPS peptide synthesis of the home-made type and the stirrer is a Flask Shaker model A5-6021. The variation of the coupling of the polyamines to the solid phase as well as the variation of the protection of the polyamines in the SPPS is monitored by the Kaiser test [Kaiser, E., Colescolt, D. L., Bossinger, C. D. and Cook, P. I. *Anal. Biochem.* 34(2), 595 (1970)].

The resin used in the examples for the SPPS is "Chlorotrityl chloride Resin" from NOVABIOCHEM.

EXAMPLES

Example 1

Synthesis of compound 1 (N-dioctadecylcarbamoylmethyl-2-{3-[4-(3-guanidinopropylamino)butylamino]propylamino}acetamide) from the compound RPR 120535 (whose preparation has been described in Patent Application WO 97/18185 incorporated into the present application by way of reference).

The synthesis step is represented in FIG. 1 of the drawings.

0.784 mmol of RPR 120535 is dissolved in 25 ml of methanol in a round-bottomed flask equipped with a magnetic stirrer bar. 10.21 mmol of triethylamine TEA are added to this solution. Then, 1.173 mmol of a solution of O-methylisourea/sulphuric acid $H_2SO_4$ in 9 ml of water are poured slowly (5 minutes) over the mixture. After the pouring, cloudiness appears. The mixture is maintained at 40° C. for 16 hours and then the solution is evaporated to dryness. The product obtained is then purified by preparative HPLC. The fractions of interest are combined and freeze-dried.

0.157 mmol of salified compound 1 is obtained, i.e. a yield of 20.1%.

$HPLC_{analytical}$: Rt=14.94 min. $^1$H NMR spectrum (400 MHz, $(CD_3)_2SO$-$d_6$, δ in ppm): 0.86 (t, J=7 Hz, 6H: $CH_3$ of the fatty chains); 1.24 (mt, 60H: central $(CH_2)_{15}$ groups of the fatty chains); 1.43 and 1.53 (2 mts, 2H each: 1 $CH_2$ of each fatty chain); 1.63 (mt, 4H: central $(CH_2)_2$ groups of the butyl); 1.81 and 1.96 (2 mts, 2H each: central $CH_2$ of the propyls); from 2.85 to 3.10 and 3.22 (2 mts, 16H in total: $NCH_2$ of the butyl—$NCH_2$ of the propyls and $NCH_2$ of the fatty chains); 3.81 (broad s, 2H: $NCH_2CON$); 4.03 (d, J=4.5 Hz, 2H: $CONCH_2CON$ of the glycyl); 7.32–7.97–8.62–8.75 and 9.02 (respectively unres. comp.-t-t-unres. comp. and unres. comp.: H corresponding to the exchangeable protons). $MH^+=863$

Example 2

Synthesis of compound 2 (2-{2-[bis(2-guanidinoethyl)amino]ethylamino}-N,N-dioctadecylacetamide) from the compound RPR 120527 (whose preparation has been described in Patent Application Wo 97/18185 incorporated into the present application by way of reference).

48 μmol of RPR 120527 are dissolved in 10 ml of methanol, and then 85 μl of DIEA (10 equivalents) and 32 mg of 1,3-bis(tert-butoxycarbonyl)-2-methyl-2-thio-pseudourea (2.3 equivalents) are added. The reaction is monitored by HPLC. After 24 hours, the solvent is evaporated and 20 ml of a TFA/dichloromethane solution 1:1 by volume are added to the residue obtained. After evaporation under vacuum, the residue is purified by preparative HPLC. The fractions of interest are mixed, frozen in liquid nitrogen and then freeze-dried. 0.035 mmol of compound 2 is thus obtained, i.e. a yield of 73%.

Analytical HPLC: Rt=16.20 min. $^1$H NMR spectrum (400 MHz, $(CD_3)_2SO$-$d_6$, δ in ppm): 0.9 (m: 6H: $CH_3$) 1.2 (m: 60H: $CH_2$) 1.6 (m: 4H: $CH_2CH_2N$) 2.7–2.9 (m: 6H: $CH_2N(CH_2)_2$) 3.0 (m: 2H: $CH_2CH_2N(CH_2)_2$) 3.2 (m: 8H: $CH_2N$) 3.8 (m: 4H: $CH_2NCOCH_2N$). $MH^+=793$

Example 3

Synthesis of compound 3 (N-ditetradecylcarbamoylmethyl-2-{3-[4-(3-guanidinopropylamino)butylamino]propylamino}acetamide) from the compound RPR 122766 (whose preparation has been described in Patent Application WO 97/18185 incorporated into the present application by way of reference).

0.784 mmol of RPR 122766 is dissolved in 25 ml of methanol in a round-bottomed flask equipped with a magnetic stirrer bar. 10.21 mmol of triethylamine TEA are added to this solution. Then, 1.173 mmol of a solution of O-methylisourea/sulphuric acid $H_2SO_4$ in 9 ml of water are poured slowly (5 minutes) over the mixture. After the pouring, cloudiness appears. The mixture is maintained at 40° C. for 16 hours and then the solution is evaporated to dryness. The product obtained is then purified by preparative HPLC. The fractions of interest are combined and freeze-dried.

0.2289 mmol of compound 3 is thus obtained, i.e. a yield of 29%.

Analytical HPLC: Rt=9.8 min. $^1$H NMR spectrum (400 MHz, $(CD_3)_2SO$-$d_6$, δ in ppm): 0.87 (t, J=7 Hz, 6H: $CH_3$ of the fatty chains); from 1.15 to 1.40 (mt, 44H: central $(CH_2)_{11}$ groups of the fatty chains); 1.46 and 1.55 (2 mts, 2H each: 1 $CH_2$ of each fatty chain); 1.63 (mt, 4H: the 2 central $CH_2$ groups of the butyl); 1.81 and 1.95 (2 mts, 2H each: central $CH_2$ of the propyls); from 2.85 to 3.10 (mt, 10H: the 2 $NCH_2$ groups of the butyl—the 2 $NCH_2$ groups of one of the 2 propyls—and 1 of the 2 $NCH_2$ groups of the other propyl); from 3.15 to 3.25 (mt, 6H: the other $NCH_2$ of the other propyl and $NCH_2$ of the fatty chains): 3.82 (unres. comp., 2H: $NCH_2CON$); 4.04 (d, J=5 Hz, 2H: $CONCH_2CON$ of the glycyl); from 7.00 to 7.60—from 8.60 to 8.75 and 9.00 (respectively broad unres. comp. and 2 unres. comp., 3H–5H and 2H: $NH_3^+CF_3COO^-$—$NH_2^+CF_3COO^-$ and =NH); 7.78 (broad t, J=5.5 Hz, 1H: N=CNH); 8.65 (unres. comp.: 1H corresponding to the CONH). $MH^+=751$

Example 4

Synthesis of compound 4 (2-{2-[bis(2-guanidinoethyl)amino]ethylamino}-N-ditetradecylcarbamoylmethylacetamide)

Step A: 10 molar excess of tris(aminoethyl)amine is dissolved in 50 ml of dichloromethane, and the solution is introduced into a-reactor containing a bromoacetyl(chloro)trityl resin (obtained beforehand by reacting bromoacetic acid with a chlorotrityl resin). The reactor is stirred for 2 hours at room temperature. The solvent is filtered and the resin is washed with 10 times 50 ml of dichloromethane and isopropanol. The Kaiser test is positive.

Step B: The resins obtained are brought into contact with an excess of 10 equivalents of 1,3-bis(tert-butoxycarbonyl)-2-methyl-e-thiopseudourea dissolved in dichloromethane, with stirring, for 24 hours. The solvent is filtered and the resin is washed with times 50 ml of dichloromethane and isopropanol. The 3-minute Kaiser test at low temperature is negative.

Step C: 50 mmol of DIEA are dissovled in 50 ml of dichloromethane, and the mixture is introduced into the reactor containing the product obtained in step B. Then, 48 mmol of di-tert-butyl dicarbonate are poured in. The reactor is stirred overnight. The next day, the Kaiser test is negative. The solvent is filtered and the resin is washed alternately with 10 times 50 ml of dichloromethane and isopropanol, twice 50 ml of methanol, and twice 50 ml of ether. The resin is then dried under a nitrogen stream. The Kaiser test is still negative.

Step D: The resins obtained in step C are introduced into a 250-ml round-bottomed flask equipped with a magnetic stirrer bar. A solution composed of 50 ml of dichloromethane and 25 ml of 1,1,1-trifluoroethan-2-ol is added thereto and the mixture is stirred for 2 hours. The solution is filtered and the resin is washed with twice 10 ml of dichloromethane. The organic phases thus obtained are combined and evaporated under vacuum. The products are then purified on silica gel (eluent: chloroform/methanol 8:2 by volume). The fractions of interest are combined and then evaporated under vacuum to give 168 mg of product having the following structure:

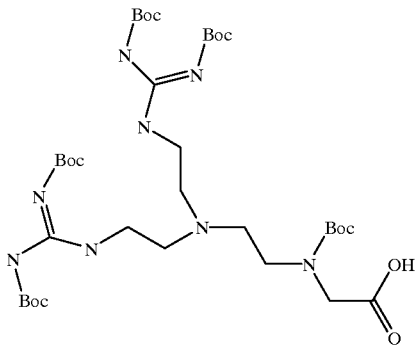

i.e. a yield of 20%. TLC: Rf=0.9. MH$^+$=789.

Step E: 9 mmol of Boc-glycinyl-di-tetradecylamide are introduced into a round-bottomed flask equiped with a magnetic stirrer bar. 30 ml of trifluoroacetic acid at 4° C. are added. The solution is stirred for one hour and the TFA is evaporated under vacuum. The product obtained is again dissolved by adding 70 ml of DMF, and then 30 mmol of TEA and 9 mmol of the acid obtained above are added. The pH is adjusted to 10, and 33 mmol of BOP are added. The solution is stirred for 2 hours and monitored by TLC. When the coupling is complete, 700 ml of a solution of potassium sulphate are added and the product is extracted with 3 times 100 ml of ethyl acetate. The organic phase is washed with 3 times 50 ml of potassium sulphate, 3 times 50 ml of sodium carbonate, and 3 times 50 ml of sodium chloride. Then, it is dried over magnesium sulphate, filtered and evaporated under vacuum. The product obtained is analysed by NMR, TLC and MS, and is deprotected with 50 ml of TFA which are added to the product obtained without prior purification. The solution is then stirred for 1 and a half hours. Finally, the TFA is evaporated and the final products are purified by semipreparative HPLC.

8.1 mmol of compound 4 are finally obtained, i.e. a yield of 90% for this last step.

Analytical HPLC: Rt=11.4 min. $^1$H NMR (400 MHz, $(CD_3)_2SO$-$d_6$, δ in ppm): 0.89 (t, J=7 Hz, 6H: $CH_3$ of the fatty chains); from 1.15 to 1.35 (mt, 44H: central $(CH_2)_{11}$ groups of the fatty chains); 1.45 and 1.54 (2 mts, 2H each: 1 $CH_2$ of each fatty chain); 2.65–2.78–3.06 and 3.23 (respectively t, J=6.5 Hz—broad t, J=6.5 Hz—unres. comp. and mt, respectively 4H-2H-2H and 8H : $NCH_2CH_2N$—the 2 $NCH_2CH_2NC$=N groups and the $NCH_2$ groups of the fatty chains); 3.83 (broad s, 2H: $NCH_2CON$); 4.04 (d, J=5 Hz, 2H: $CONCH_2CON$ of the glycyl); 7.34 (broad unres. comp., =NH and $NH_2$); 7.61 (t, J=5.5 Hz, 2H: NH); 8.65 (t, J=5 Hz, 1H: NH); 8.75 (unres. comp.: NH). MH$^+$=737

The glycinyl-di-tetradecylamide used in step E is obtained beforehand in the following manner: 10 mmol of glycine protected by Boc substituents and 10 mmol of di-tetradecylamine are introduced into a 250 ml round-bottomed flask. 100 ml of chloroform are added thereto and the mixture is stirred until complete dissolution is obtained. 30 mmol of TEA and 33 mmol of BOP are then added. The pH is maintained at 10 with triethylamine. The reaction is stirred for 2 hours. When the reaction, monitored by TLC, is complete, the chloroform is evaporated. A solid is obtained which is again dissolved in 300 ml of ethyl acetate. The organic phase is then washed with 4 times 100 ml of potassium sulphate, 4 times 100 ml of sodium carbonate, and 4 times 100 ml of sodium chloride. Then, the organic phase is dried over magnesium sulphate, filtered and evaporated under vacuum. The product obtained is analysed by TLC, NMR and MS, and is used without further purification.

Example 5

Synthesis of compound 5 (N-ditetradecylcarbamoylmethyl-2-{(3-guanidinopropyl)-[4-(3-guanidinopropylamino)butyl]amino}acetamide) The procedure is carried out in the same manner as above for compound 4, but starting with spermine as starting polyamine, to give the acid having the following structure:

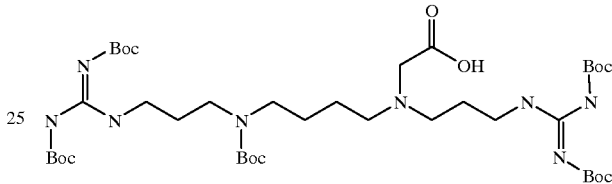

After having been cleaved from the resin, this residue is purified on silica gel (eluent: chloroform/methanol 8:2 by volume). The fractions of interest are mixed and then evaporated under vacuum to give 0.69 mmol of the said molecule, i.e. a yield of 50%.

TLC: Rf=0.5. MH$^+$=845.

Compound 5 is obtained by coupling between the acid previously synthesized and the glycinyl-di-tetradecylamide according to the same method as that described in Example 4. The glycinyl-di-tetradecylamide is also obtained in the same manner as above.

0.65 mmol of compound 5 is thus obtained, i.e. a yield of 94% for this step.

Analytical HPLC: Rt=10.1 min. $^1$H NMR spectrum (400 MHz, $(CD_3)_2SO$-$d_6$, at a temperature of 393 K, δ in ppm): 0.92 (t, J=7 Hz, 6H: $CH_3$ of the fatty chains); from 1.25 to 1.45 (mt, 44H: central $(CH_2)_{11}$ groups of the fatty chains); 1.57 (mt, 4H: the 2 central $CH_2$ groups of the butyl); 1.57 and 1.67 (2 mts, 2H each: 1 $CH_2$ of each fatty chain); 1.74 and 1.91 (2 mts, 2H each: central $CH_2$ of the propyls) 2.62–2.85—from 3.20 to 3.35 (3 mts, 16H in total: the $NCH_2$ groups—the $CH_2NC$=N groups and $NCH_2$ groups of the fatty chains); 3.17 (s, 2H: $NCH_2CON$); 4.02 (d, J=5 Hz, 2H: $CONCH_2CON$ of the glycyl); 6.89—from 7.30 to 7.55 and 7.65 (respectively unres. comp.—broad unres. comp. and unres. comp.: the exchangeable H atoms). MH$^+$=845.

Example 6

Synthesis of compound 6 (2-{3-[{4-[bis(3-guanidinopropyl)amino]butyl}-(3-guanidinopropyl)amino]-propylamino}-N-ditetradecylcarbamoylmethylacetamide) The procedure is carried out in the same manner as above for compounds 4 and 5, but starting with N',N-N',N'-(tetraaminopropyl)butylenediamine as starting polyamine, to give the acid having the following structure:

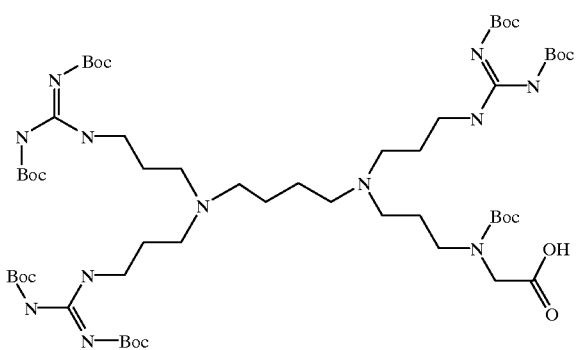

After having been cleaved from the resin, the residue obtained is purified on silica gel (eluent: chloroform/methanol 8:2 by volume). The fractions of interest are mixed and then evaporated under vacuum to give 0.099 mmol of product, i.e. a yield of 20%.

TLC: Rf=0.3. MH$^+$–1201.

Compound 6 is obtained by coupling between the acid previously synthesized and the glycinyl-di-tetradecylamide according to the same method as that described in Example 4. The glycinyl-di-tetradecylamide is also obtained in the same manner as above.

0.09 mmol of compound 6 is thus obtained, i.e. a yield of 90% for this step.

Analytical HPLC: Rt=11.2 min. $^1$H NMR spectrum (400 MHz, $(CD_3)_2SO$-$d_6$, with addition of a few drops of $CD_3COOD$-$d_4$, δ in ppm): 0.87 (t, J=7 Hz, 6H: $CH_3$ of the fatty chains); from 1.20 to 1.40 (mt, 44H: central $(CH_2)_{11}$ groups of the fatty chains); 1.45 and 1.54 (2 mts, 2H each: 1 $CH_2$ of each fatty chain); 1.67 (mt, 4H: central $CH_2$ groups of the butyl); from 1.80 to 2.10 (mt, 8H: central $CH_2$ of the propyls); from 2.95 to 3.30 (mt, 20H: the $NCH_2$ groups of the propyls and the $NCH_2$ groups of the butyl); from 3.15 to 3.30 (mt, 4H, the $NCH_2$ groups of the fatty chains); 3.84 (s, 2H: $NCH_2CON$); 4.05 (s, 2H: $CONCH_2CON$ of the glycyl). MH$^+$=949.

Example 7

Use of Compound 1 for the in Vitro Transfection of Genetic Material

Genetic Material Used:

The nucleic acid used is the plasmid pXL2774 (WO 97/10343) comprising the gene encoding luciferase under the control of the human cytomegalovirus (CMV) promoter.

The nucleic acid solutions are diluted to 20 μg/ml in physiological saline (0.15 M sodium chloride NaCl).

Transfection Solutions (prepared immediately before use)

The products described in the invention are dissolved in water at a concentration varying from 60 to 240 μM and mixed volume for volume with the DNA solution; the final saline concentration is 75 mM.

Transfection

The cells are cultured under appropriate conditions in 24-well microplates (2 cm²/well) and are transfected while they are in the exponential growth phase and at 50–70% confluence.

The cells are washed with twice 500 μl of medium free of serum proteins and grown again either in serum-free medium (transfection in the absence of serum), or in complete medium (transfection in the presence of serum). 50 μl of transfectant mixture [i.e. 0.5 μg DNA/well] are added to the cells [3 wells/condition DNA vector]. When the cells are transfected in the absence of serum, the growth medium is supplemented 2 hours after transfection with the appropriate quantity of serum.

The transfection efficiency is evaluated 48 hours after the transfection by measuring the expression of luciferase according to the recommendations given for the use of the Promega kit [Luciferase Assay System]. The toxicity of the transfectant mixtures is estimated by a measurement of the protein concentrations in the cell lysates.

Results

Compound 1 was used in comparison with the cationic lipid RPR120535 (TFA salt) [described in patent application WO 97/18185 incorporated into the present application by way of reference] as DNA vector to transfect three different cell lines: NIH3T3 cells, HepG2 cells and HeLa cells. For these three cell types, no significant toxicity was detected for compound 1 whose preparation is described in Example 1. The transfection efficiency for compound 1 and for the cationic lipid for comparison in the three cell types is represented in FIG. 2, for nmol of compound/μg of DNA ratios of between 3 and 12.

From FIG. 2, it is possible to deduce that the maximum transfection efficiency is obtained for a ratio of 6 nanomoles cationic lipid/μg of DNA for the NIH3T3 cells and for a ratio of 9 nanomoles cationic lipid/μg of DNA for the HeLa or HepG2 cells. For transfection in the absence of serum, the expression levels obtained in the HeLa or HepG2 cells are 2 to 4 times higher for compound 1 than for the product tested in comparison.

FIG. 3 represents the transfection efficiency for the compound 1/DNA complexes in comparison with the same reference cationic lipid as above (RPR120535) complexed with the DNA. The white bars represent the transfection efficiency for the nucleolipid complexes in the absence of serum for 2 hours. The black bars represent the transfection efficiency for the nucleolipid complexes in the presence of serum.

From FIG. 3, it is thus possible to demonstrate one of the specific advantages of the transfection agents according to the invention. Indeed, it is observed that the transfection levels with or without serum proteins are the same in the case of compound 1 of the invention, whereas with the cationic lipid for comparison, a strong inhibition is observed due to the presence of the serum proteins. This constitutes a particularly advantageous property for transfections in vivo.

Example 8

Use of Compounds 2, 3, 5 and 6 for the in Vitro Transfection of Genetic Material Genetic Material Used:

The nucleic acid used is the plasmid pXL3031 containing the gene encoding luciferase under the control of the human cytomegalovirus (CMV) promoter. This plasmid pXL3031 is represented in FIG. 15. It was isolated according to standard protocols known to persons skilled in the art, and in particular according to Maniatis T., Fritsch E. F. and Sambrook J., *Methods in Molecular Biology: a Laboratory Manual*, 1982, pp. 83–94, Cold Spring Harbor Lab., NY. More concretely, the methods used are the alkaline lysis method and caesium chloride gradient purification.

Transfection:

The cells are cultured under appropriate conditions in 24-well microplates. After growing overnight, each well contains about 100,000 cells.

The transfectant mixture, which contains 1 µg of DNA in 0.5 ml of DMEM, is introduced into each well in the absence of serum. 5 hours after the transfection, the growth medium is supplemented with the appropriate quantity of serum (DMEM and foetal calf serum, 10%). The cellular lysates are recovered 24 hours after the transfection, and the transfection efficiency is calculated by measuring the expression of luciferase according to the recommendations given for the use of the Promega kit (Luciferase Detection Kit).

Results:

The transfection levels are represented in FIGS. 4, 5, 6 and 7.

Each time, the transfection efficiency was measured for the lipid in the form of micelles, and mixed with a colipid (DOPE or cholesterol). From these tables, it is possible to deduce that the transfection levels are very high, even at very low charge ratios, with the beneficial consequences resulting therefrom on toxicity. This constitutes one of the advantages of the compounds of the invention. Indeed, with the cationic lipids not containing any amidine function(s), it is often necessary to use very high charge ratios in order to obtain such transfection levels, which in general causes increased toxicity.

Example 9

Study of the Affinity of Compounds 2, 3, 5 and 6 for DNA

The nucleic acid used is the plasmid pXL3031, as described in the preceding example.

The complexes are prepared at concentrations of 0.25 mg of DNA/ml with an appropriate quantity of lipid as defined in the present invention in the desired charge ratio. The complex is prepared in a medium containing 5% glucose and a 20 mM solution of sodium chloride. 50 µl of nucleolipid complex are then diluted 20-fold in 950 µl of solution containing 5% glucose and a 20 mM solution of sodium chloride.

The size of the complexes was determined by measuring the hydrodynamic diameter by dynamic light scattering with the aid of a Coulter N4+ apparatus.

For all the compounds, 3 distinct physicochemical phases were demonstrated depending on the charge ratio:

Phase A for which the DNA is not saturated with the cationic lipid, that is to say that there is still naked DNA remaining in the mixture, which means that the DNA is not completely protected by the lipid and can therefore be subjected to degradation by enzymes. The complexes formed are negatively charged overall, which makes the crossing of cell membranes difficult. It is thus preferable for the values not to be situated in this region in order to transfect the DNA.

Phase B for which the DNA is completely saturated with the cationic lipid and the complexes are neutral or slightly positive overall. The ionic repulsions being maximum, this phase is unstable. A phenomenon of "cross-linking" may occur, leading to precipitation of the complexes. The complexes in this state cannot therefore be used as injection.

Phase C for which the DNA is oversaturated with the lipid and the complexes are therefore positive overall. The DNA is therefore completely protected by the lipid and its passage across the cell membrane (negative overall) is facilitated. The complexes in phase C are therefore particularly suitable for use for the transfer of nucleic acids into cells.

The tables indicating the phase in which the complexes are situated as a function of the charge ratio are represented in FIGS. 8, 9, 10 and 11.

The tables in FIGS. 8, 9, 10 and 11 compare the phases as a function of the charge ratios between the compounds of the invention and their amine-containing analogues, that is to say the cationic lipids whose amidine or guanidine function is replaced by an amino function. It is observed that phase B is shifted towards much lower charge ratios. Thus, the incorporation of amidine functions into the cationic head contributes to the increase in the affinity of the compounds for DNA. This constitutes an important property of the compounds of the invention because the complexes which they form with DNA may be used in phase C without as a result being at excessively high charge ratios, with the beneficial effects which result therefrom on toxicity.

The affinity of the compounds of the invention for DNA was also evaluated with the aid of the measurement of the reduction in fluorescence after addition of ethidium bromide. Indeed, the replacement of the ethidium bromide of the DNA by the lipid is an indication of binding to the DNA.

Thus, 4 µl of a solution of ethidium bromide 1 mg/ml are added to the complexes prepared, and then the fluorescence is measured at an excitation wavelength of 260 nm and at an emission wavelength of 590 nm. The fluorescence obtained for the DNA alone is defined as being 100%.

The results are indicated in the tables in FIGS. 12, 13 and 14. These results indicate that the compounds of the invention exhibit very good affinity for DNA, which constitutes a particularly advantageous property of the compounds of the invention.

What is claimed is:

1. A compound comprising lipopolyamine in D, L or DL form, as well as its salts, of general formula (I):

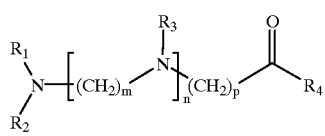

in which:

$R_1$, $R_2$ and $R_3$ represent, independently of each other, a hydrogen atom or a group —$(CH_2)_q$—NRR' with q being an integer from 1 to 6 inclusive, the values of q being independent of each other between the different groups $R_1$, $R_2$ and $R_3$, and R and R' represent, independently of each other, a hydrogen atom or a group of formula (II):

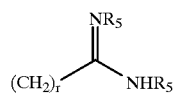

in which r is an integer which may vary from 0 to 6 inclusive, and the $R_5$ groups represent, independently of each other, a hydrogen atom or a hydrocarbon residue, it being understood that at least one of the groups $R_1$, $R_2$ and $R_3$ contains at least one group of formula (II);

m and n represent, independently of each other, an integer which may vary from 1 to 6 inclusive and, when n is greater than 1, m may have different values and $R_3$ different meanings within the general formula (I), p represents an integer which may vary between 1 and 6 inclusive, and $R_4$ represents a group of general formula (III):

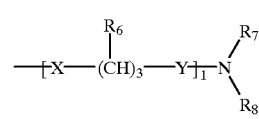

in which:

$R_7$ and $R_8$ represent, independently of each other, a hydrogen atom or a lipophilic group, at least one of the groups $R_7$ and $R_8$ being different from hydrogen, t is an integer chosen from 0 to 10 inclusive with $R_6$, X, Y and s may have different meanings within the different units [X-$(CHR_6)_s$—Y] when t is an integer greater than 1, X represents an oxygen or sulphur atom or an amine or alkylamino group, the alkyl substituent being linear or branched and containing 1 to 8 carbon atoms, Y represents a carbonyl group or a methylene group, $R_6$ represents a hydrogen atom or a natural amino acid side chain, substituted where appropriate and s represents an integer varying from 1 to 10 inclusive with, when s is equal to 1, $R_6$ representing a natural amino acid side chain optionally substituted, and when s is greater than 1, $R_6$ representing a hydrogen atom.

2. The compound according to claim 1, wherein the $R_5$ group of formula (II) is a hydrogen atom or an aliphatic or aromatic hydrocarbon residue that is optionally halogenated.

3. The compound according to claim 2, wherein one of the $R_5$ groups of formula (II) is a hydrogen atom and the other is an aliphatic hydrocarbon residue containing 1 to 10 carbon atoms or an aromatic hydrocarbon residue preferably chosen from benzyl and its derivatives.

4. The compound according to claim 2, wherein the two $R_5$ groups of formula (II) are hydrogen atoms.

5. The compound according to claim 1, wherein, when $R_1$, $R_2$ and/or $R_3$ are different from hydrogen and comprise the formula (II), q is equal to 2 or 3 and r is equal to 0.

6. The compound according to claim 1, wherein, in the general formula (I), m is equal to 2, 3, or 4.

7. The compound according to claim 1, wherein, in formula (III), at least one of the groups $R_7$ and $R_8$ is a lipophilic group composed of one or more aliphatic fatty chains, a steroid derivative, a natural or synthetic lipid, or a combination of these.

8. The compound according to claim 7, wherein the lipophilic group is a linear or branched, saturated or unsaturated aliphatic radical containing 5 to 22 carbon atoms that is optionally halogenated.

9. The compound according to claim 7, wherein the lipophilic group is a steroid derivative selected from the group consisting of cholesterol, cholestanol, 3-α-5-cyclo-5-α-cholestan-6-β-ol, cholic acid, cholesteryl formate, cholestanyl formate, 3α,5-cyclo-5α-cholestan-6β-yl formate, cholesterylamine, 6-(1,5-dimethylhexyl)-3a,5a-dimethylhexadecahydrocyclopenta[a]cyclopropa[2,3]-cyclopenta[1,2-f]naphthalen-10-ylamine, and cholestanylamine.

10. The compound according to claim 7, wherein the lipophilic group is a group $(CH2)_u$—NH—$R_9$ in which u is an integer between 2 and 6 inclusive and $R_9$ is an acyl radical selected from the group consisting of cholesteryl formate, arachidonyl, and cholic acid.

11. The compound according to claim 1, wherein the two groups $R_7$ and $R_8$ are lipophilic groups.

12. The compound according to claim 11, wherein the two groups $R_7$ and $R_8$ are an aliphatic chain containing 5 to 22 carbon atoms.

13. The compound according to claim 12, wherein the aliphatic chain of the two groups $R_7$ and $R_8$ contains 12 and 22 carbon atoms.

14. The compound according to claim 1, wherein $R_1$ comprises a group of formula (II) and wherein $R_2$ and $R_3$ are hydrogen atoms.

15. The compound according to claim 1, wherein $R_1$ and $R_2$ each comprise a group of formula (II) and wherein $R_3$ is a hydrogen atom.

16. The compound according to claim 1, wherein $R_1$ and $R_3$ each comprise a group of formula (II) and wherein $R_2$ is a hydrogen atom.

17. The compound according to claim 1, wherein $R_1$, $R_2$ and $R_3$ each comprise a group of formula (II).

18. The compound according to claim 1, wherein the compound is combined with an extra- or intracellular targeting component.

19. The compound according to claim 18, wherein the compound incorporates the extra- or intracellular targeting component at the level of the $R_6$ amino acid side chain.

20. The compound according to claim 1, wherein the compound incorporates a marker selected from the group consisting of biotin, rhodamine, folate, a linear peptide, a cyclic peptide, and a pseudopeptide sequence comprising the Arg-Gly-Asp epitope, wherein the marker is incorporated at the level of the $R_6$ amino acid side chain of the compound.

21. The compound according to claim 1, wherein the compound is chosen from the compounds of the following formulae in which $R_4$ and $R_5$ have the meanings given in claim 1:

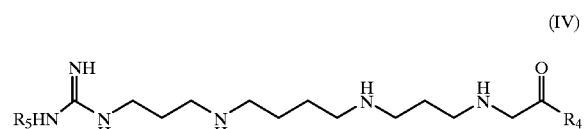
(IV)

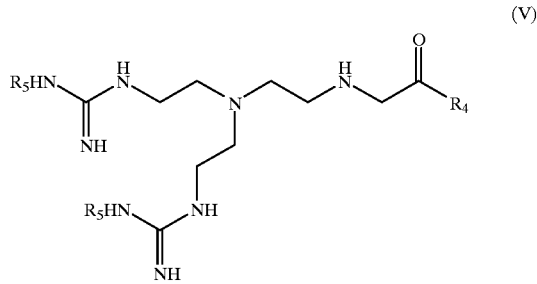
(V)

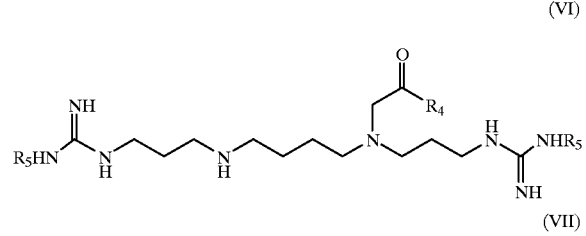
(VI)

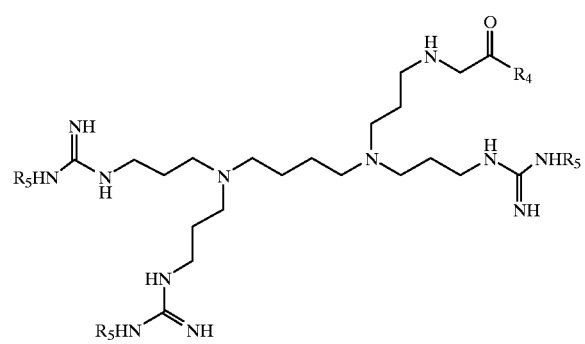
(VII)

22. The compound according to claim 1, wherein the compound is selected from the group consisting of:

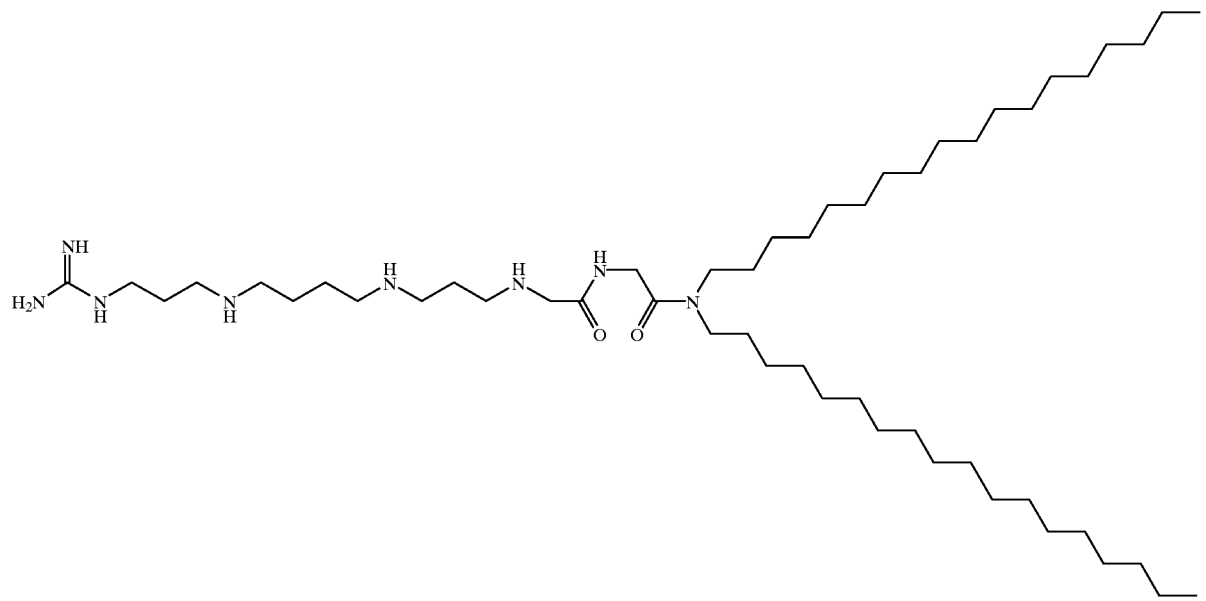
Compound 1
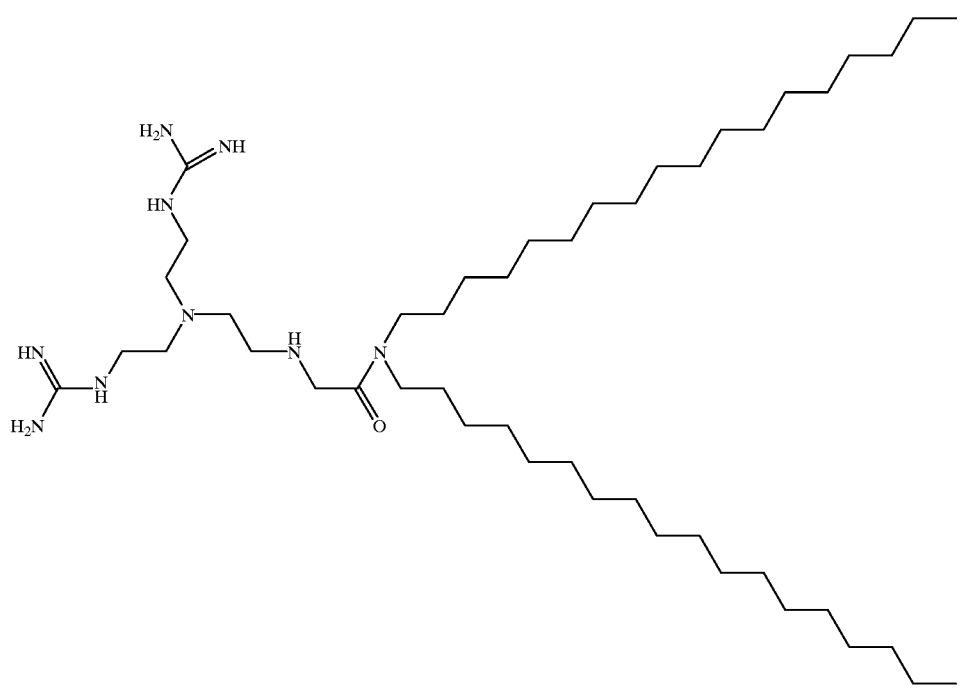
Compound 2
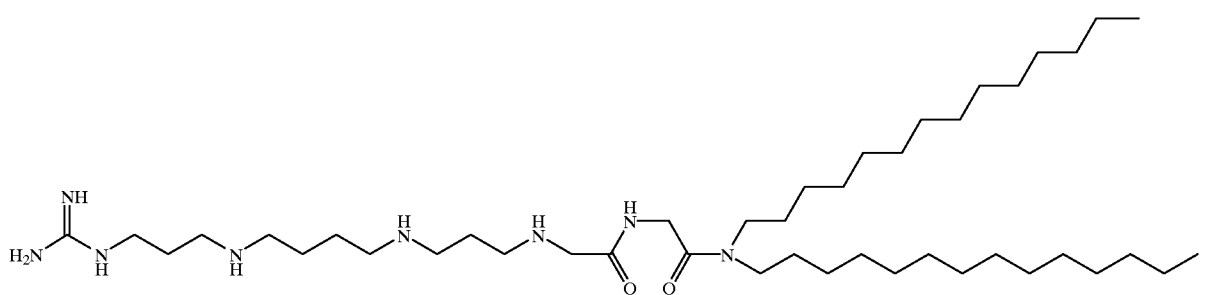
Compound 3

-continued

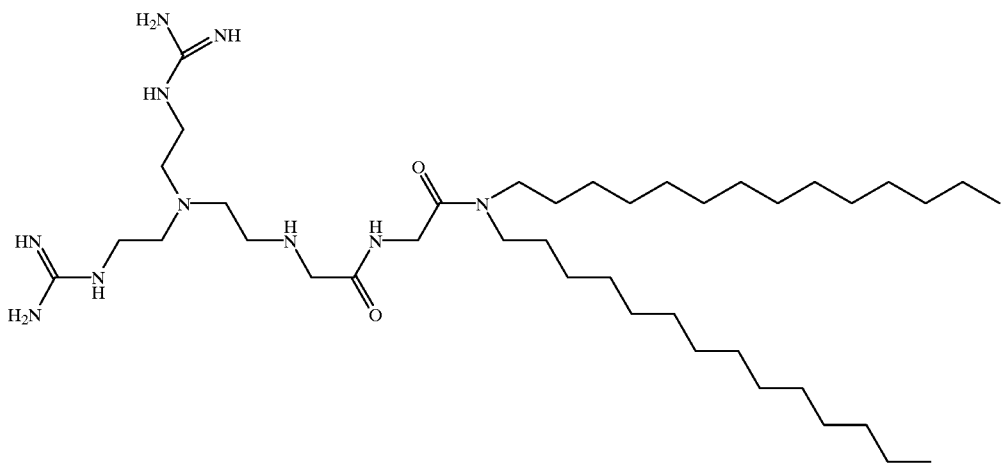
Compound 4

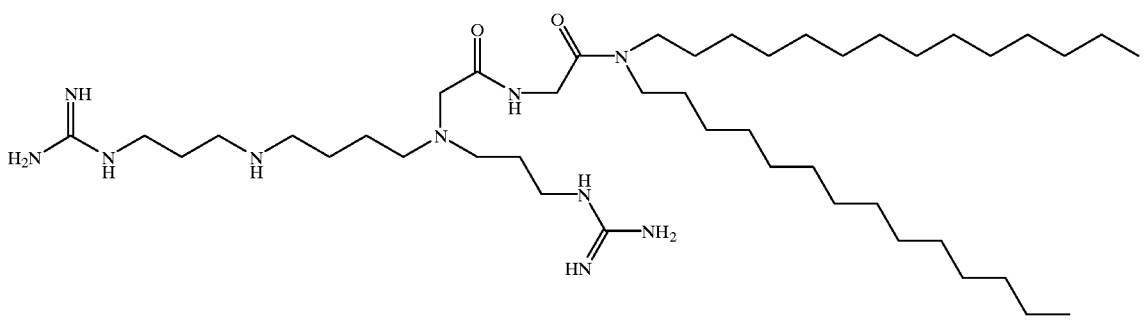
Compound 5

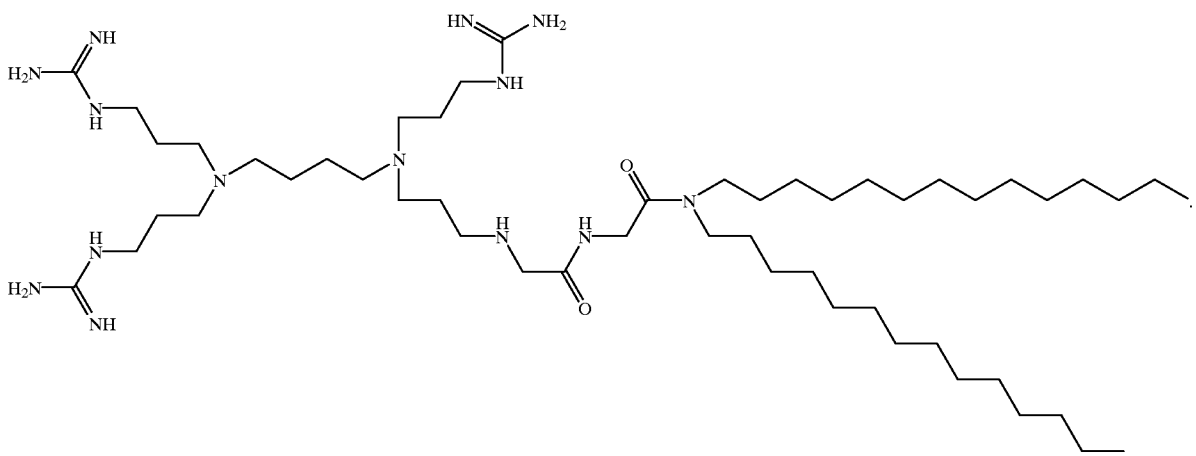
Compound 6

23. A composition comprising the compound according to claim 1 and a nucleic acid.

24. The composition according to claim 23, wherein the composition further comprises an adjuvant.

25. The composition according to claim 24, wherein the adjuvant is a neutral lipid.

26. The composition according to claim 25, wherein the neutral lipid is a lipid containing two fatty chains.

27. The composition according to claim 25, wherein the neutral lipid is a natural or synthetic lipid that is zwitterionic or lacking ionic charge under physiological conditions.

28. The composition according to claim 27, wherein the natural or synthetic lipid is selected from the group consisting of dioleoylphosphatidylethanolamine (DOPE), oleoylpalmitoylphosphatidylethanolamine (POPE), di-stearoylphosphatidylethanolamine, di-palmitoylphosphatidylethanolamine, di-myristoylphosphatidylethanolamine, as well as their derivatives that are N-methylated 1 to 3 times; phosphatidylglycerol, diacylglycerol, glycosyldiacylglycerol, cerebroside, galactocerebroside, sphingolipid, sphingomyelin, asialoganglioside, asialoGM1, and asialoGM2.

29. The composition according to claim 24, wherein the adjuvant is a compound that is involved at the level of condensation of the nucleic acid.

30. The composition according to claim 24, wherein the adjuvant is either derived as a whole or in part from a protamine, a histone, or a nucleolin and/or from one of their derivatives, or consists as a whole or in part of peptide units (KTPKKAKKP)(SEQ ID NO:1) and/or (ATPAKKAA) (SEQ ID NO:2), wherein the number of units may vary between 2 and 10 and may be repeated.

31. The composition according to claim 23, wherein the composition further comprises a targeting component.

32. The composition according to claim 23, wherein the composition further comprises a pharmaceutically acceptable vehicle for an injectable formulation.

33. The composition according to claim 23, wherein the composition further comprises a pharmaceutically acceptable vehicle for application to skin and/or mucous membranes.

34. A method of preparing a compound according to claim 1, wherein the method comprises forming an amidine group on by reacting a thio or oxo derivative of urea with a lipopolyamine or grafting a polyaminoamidine on a lipid by peptide coupling.

35. A method of transferring a nucleic acid into a cell, wherein the method comprises the following steps:

(1) bringing the nucleic acid into contact with the compound according to claim 1 and, if appropriate, with an adjuvant and/or targeting component to form a complex, and (2) bringing the cell into contact with the complex formed in (1).

* * * * *